United States Patent [19]
Pennington et al.

[11] Patent Number: 6,038,718
[45] Date of Patent: Mar. 21, 2000

[54] SURGICAL TABLE

[75] Inventors: Donald R. Pennington, New Paris; Keith A. Stickley, Greenville; Cyril F. Reesby, Troy, all of Ohio

[73] Assignee: Midmark Corporation, Versailles, Ohio

[21] Appl. No.: 08/290,384

[22] Filed: Aug. 15, 1994

[51] Int. Cl.[7] .................................... A47B 7/02
[52] U.S. Cl. ................................ 5/618; 5/608
[58] Field of Search .............................. 5/614, 613, 616, 5/618, 621, 622, 623, 624; 292/165, 146, 150

[56] References Cited

U.S. PATENT DOCUMENTS

| | | |
|---|---|---|
| 1,650,327 | 11/1927 | Conrad . |
| 2,120,732 | 6/1938 | Comper et al. . |
| 2,306,031 | 12/1942 | Anderson et al. . |
| 2,538,993 | 1/1951 | Travis ........................................ 5/618 |
| 2,605,151 | 7/1952 | Shampaine . |
| 3,041,121 | 6/1962 | Comper . |
| 3,215,834 | 11/1965 | Tayman . |
| 3,281,141 | 10/1966 | Smiley et al. . |
| 3,355,163 | 11/1967 | Leinassar ................................... 5/624 |
| 3,411,766 | 11/1968 | Lanigan . |
| 3,452,977 | 7/1969 | Ryman . |
| 3,724,004 | 4/1973 | Behrens . |
| 3,754,749 | 8/1973 | Lyon et al. . |
| 3,851,870 | 12/1974 | Cook . |
| 3,868,103 | 2/1975 | Pageot et al. . |
| 3,905,591 | 9/1975 | Schorr et al. . |
| 3,967,128 | 6/1976 | Smulewicz . |
| 3,997,792 | 12/1976 | Conrad et al. . |
| 4,148,472 | 4/1979 | Rais et al. . |
| 4,186,917 | 2/1980 | Rais et al. . |
| 4,287,422 | 9/1981 | Kuphal et al. . |
| 4,464,780 | 8/1984 | Ruiz . |
| 4,501,414 | 2/1985 | Mason et al. . |
| 4,589,124 | 5/1986 | Ruiz . |
| 4,665,574 | 5/1987 | Filips et al. . |
| 4,761,000 | 8/1988 | Fisher et al. . |
| 4,826,221 | 5/1989 | Harmon ................................... 292/150 |
| 4,865,303 | 9/1989 | Hall . |
| 4,872,657 | 10/1989 | Lussi . |
| 4,913,413 | 4/1990 | Raab ............................................ 5/624 |
| 4,956,592 | 9/1990 | Schulte et al. . |
| 4,995,067 | 2/1991 | Royster et al. . |
| 5,016,268 | 5/1991 | Lotman . |
| 5,157,787 | 10/1992 | Donnellan ................................. 5/614 |
| 5,166,968 | 11/1992 | Morse . |
| 5,231,719 | 8/1993 | Schnelle ..................................... 5/614 |
| 5,279,011 | 1/1994 | Schnelle ..................................... 5/616 |
| 5,345,632 | 9/1994 | Langenaeken et al. . |
| 5,564,663 | 10/1996 | Cook ........................................... 5/622 |

OTHER PUBLICATIONS

Chicmate General Surgical Table (Brochure) by Kirschner Chick Surgical Systems.

Chick 702 Orthopedic & Surgical Operating Table (Brochure) by Kirschner Chick Orthopedic Products.

*Primary Examiner*—Michael J. Milano

[57] ABSTRACT

A surgical table including a control system for facilitating manipulation of the table top when a patient is a normal and a reversed position. The table includes moveable table top sections whereby the table may be reconfigured from a normal configuration for receiving a patient with the patient's head at a head end of the table to a reversed configuration with the patient's head located at the foot end of the table. The controller is adapted to sense the configuration of the table and automatically reverse selectable functions for movement of the table when the table is in the reverse configuration.

46 Claims, 14 Drawing Sheets

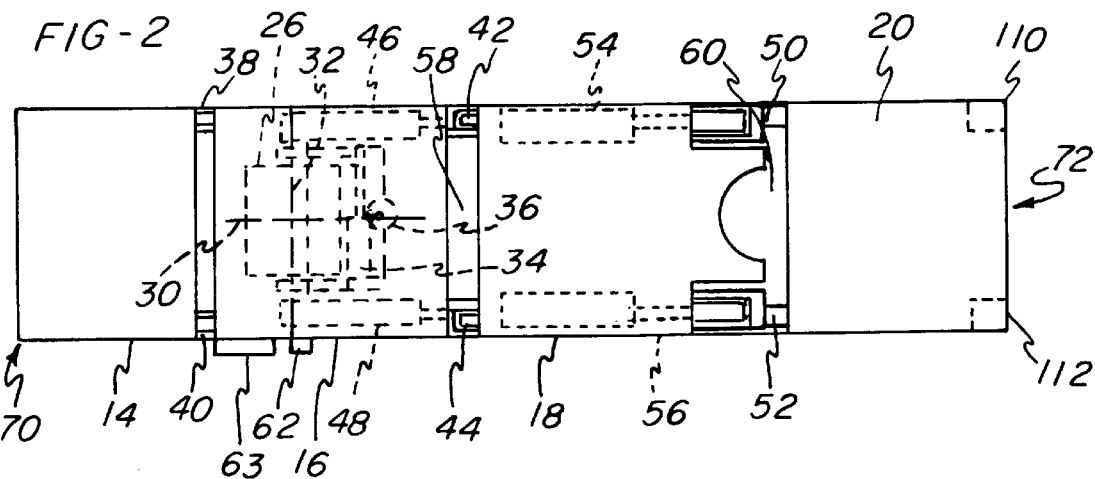
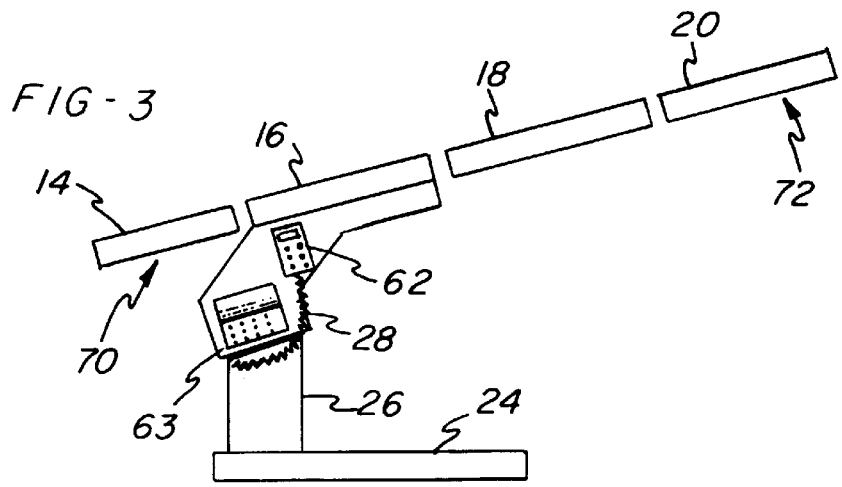
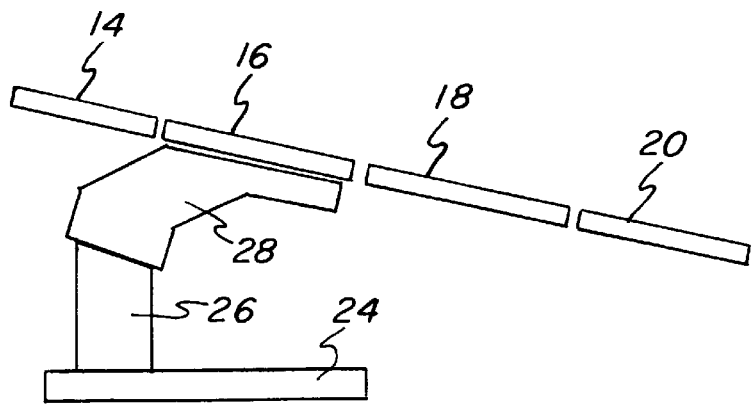

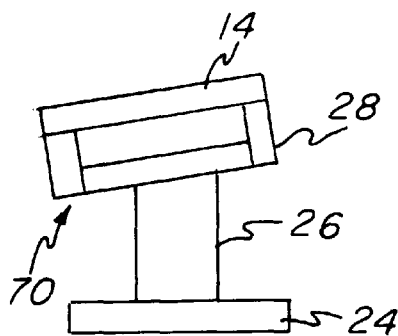
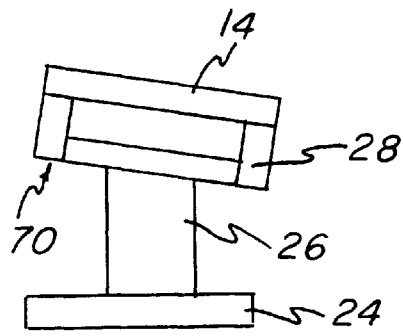
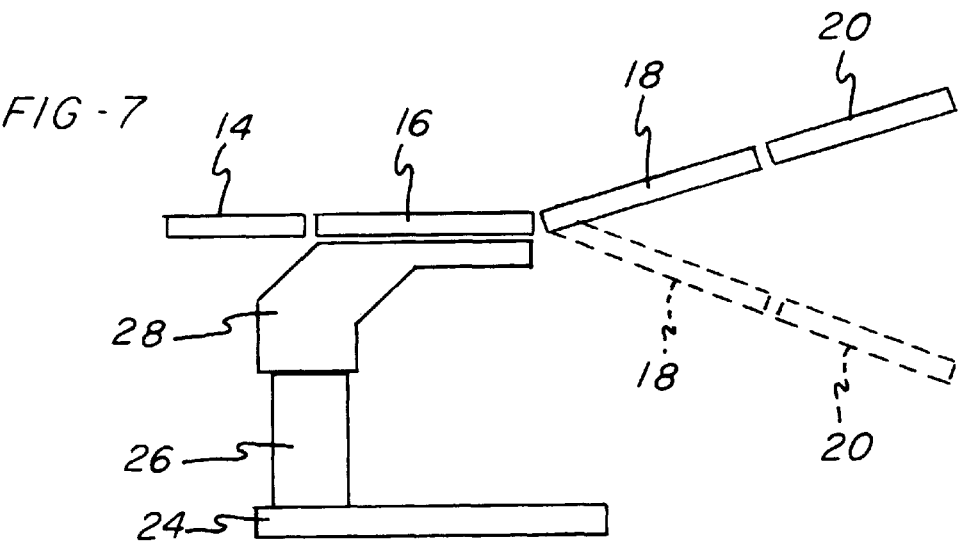
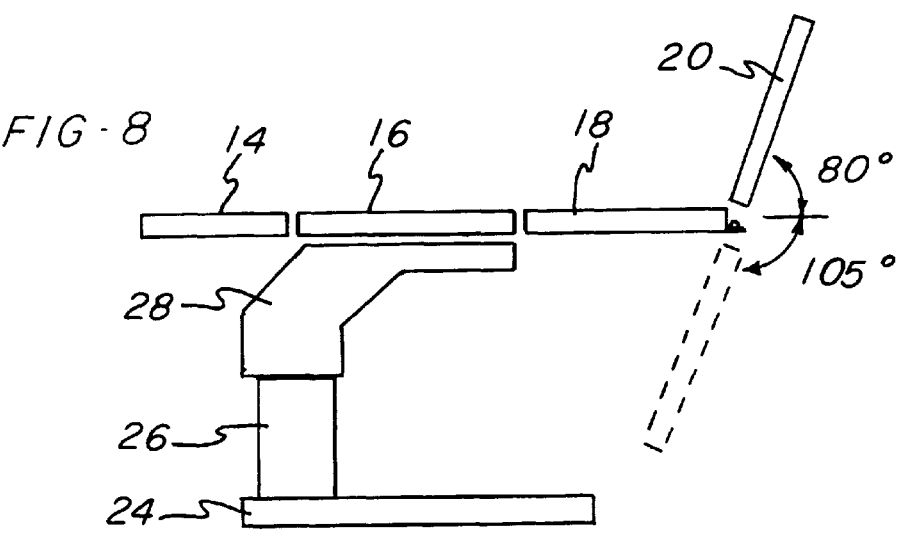

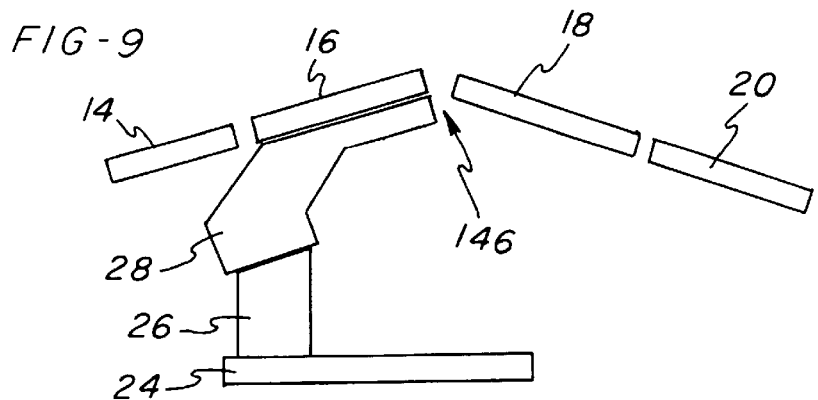
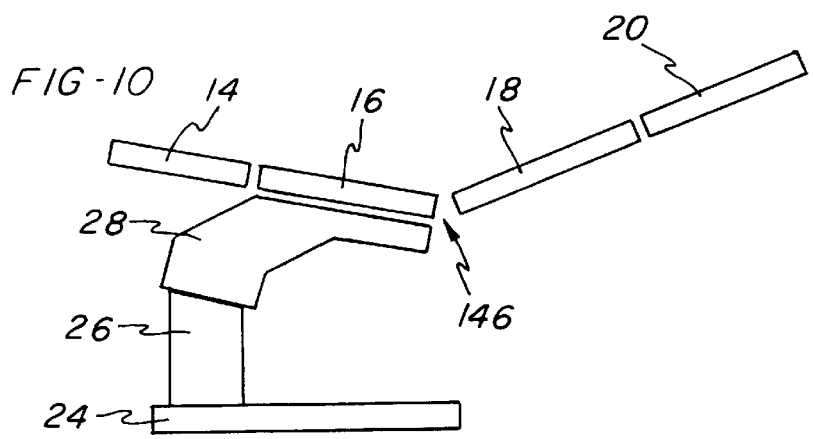
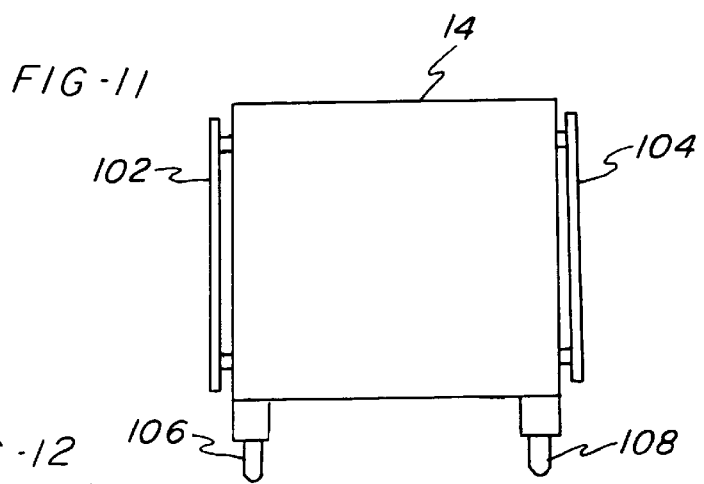
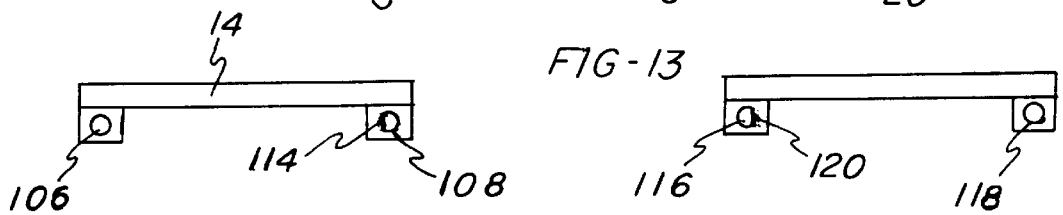

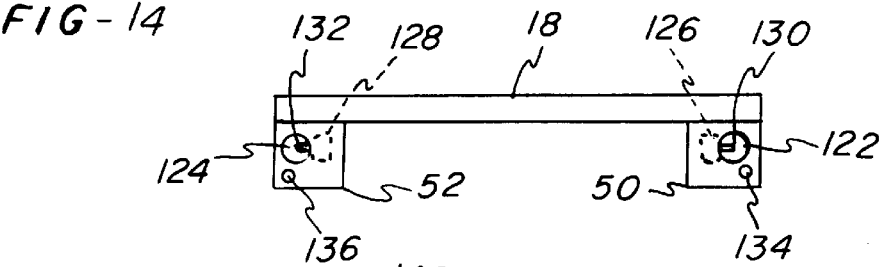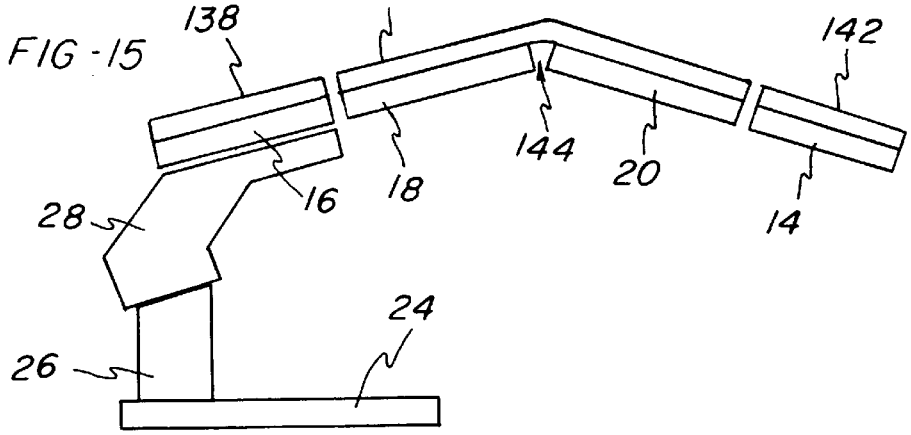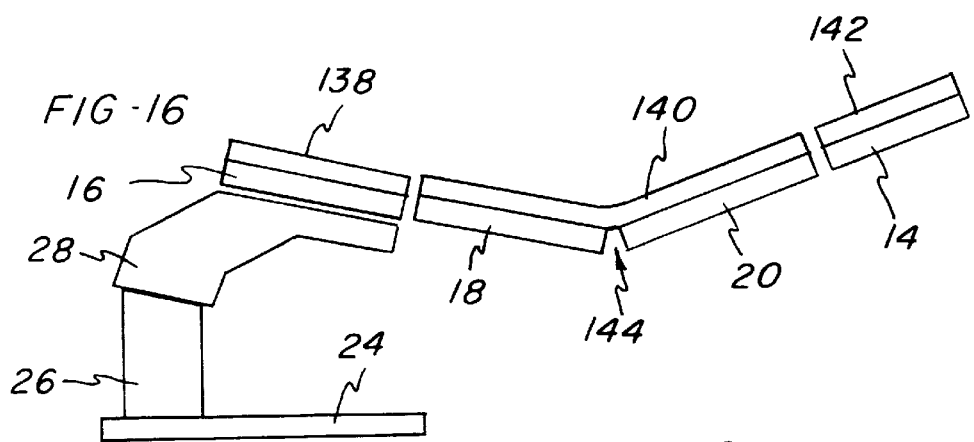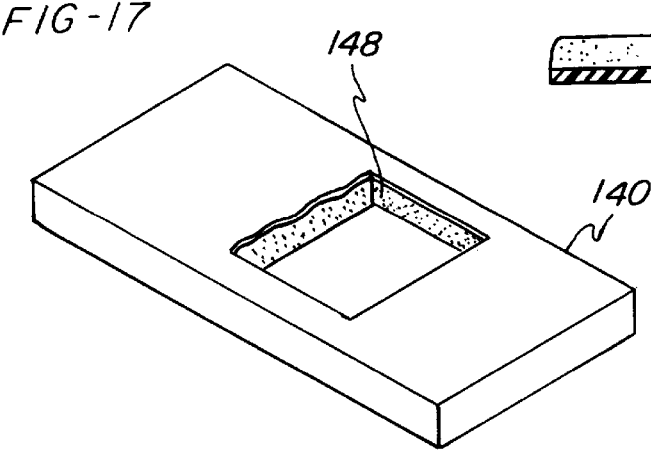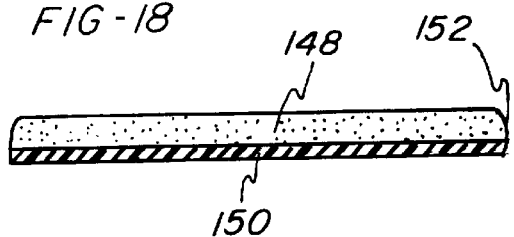

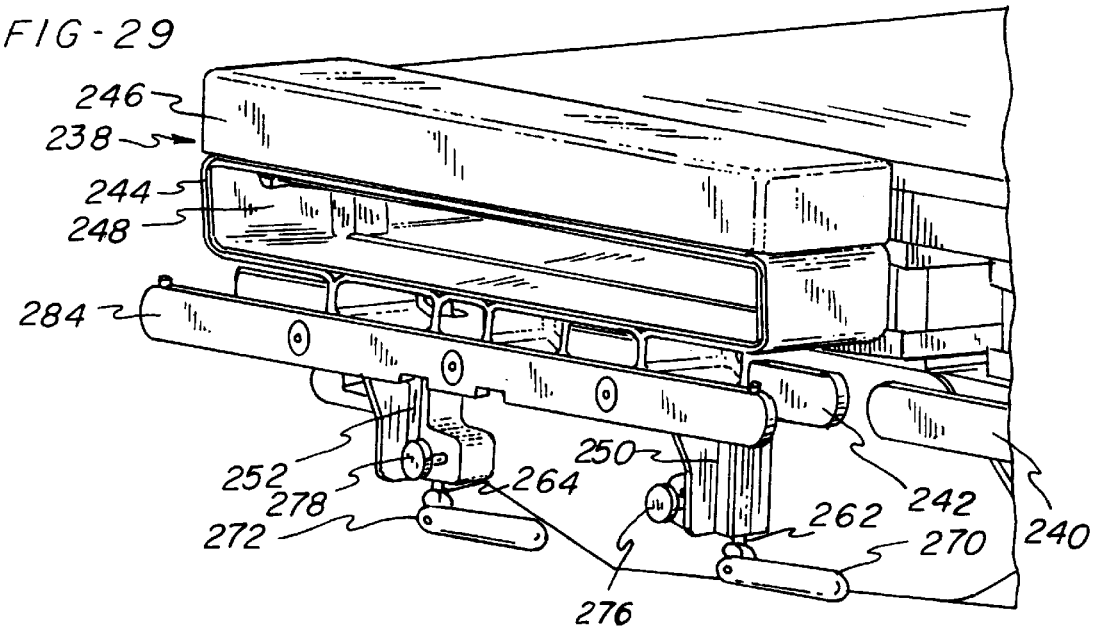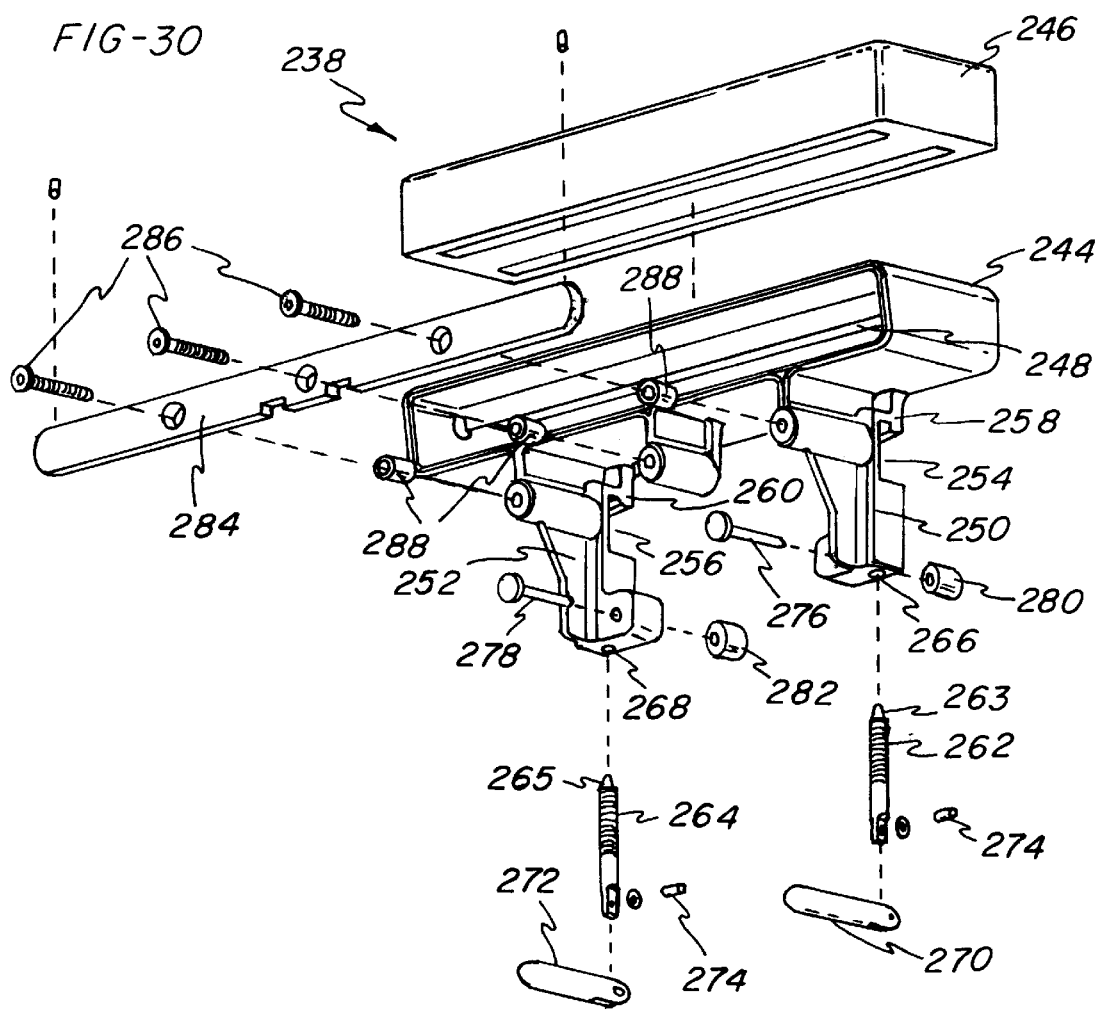

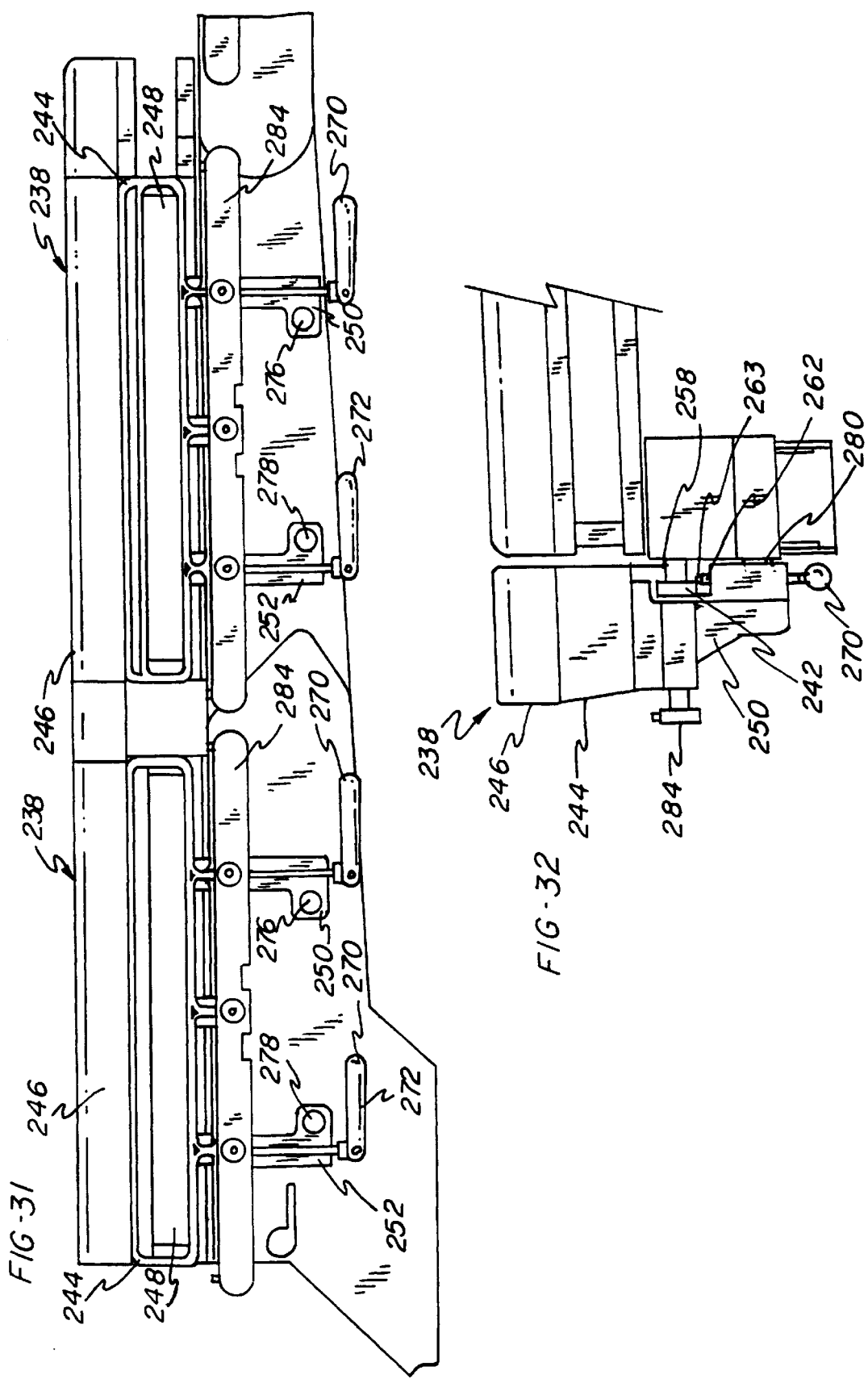

SURGICAL TABLE

BACKGROUND OF THE INVENTION

1. Field of the Invention

The present invention relates to surgical tables, and more particularly, to a surgical table having an articulated table top and an actuator system and controller for providing improved control in moving a patient to desired positions.

2. Description of Related Prior Art

Various surgical tables having articulated table tops have been developed to meet the growing demand of surgical tables which may be used for a plurality of different operations. Among the functions desirable for a surgical table are the ability to raise and lower the patient support surface, provide lateral tilting of the patient support surface to the left and right, provide a pivoting of a seat section independently of a back section, provide pivoting of a leg section independently of the seat section, movement of the patient support surface into the trendelenburg and reverse trendelenburg positions, and movement of the patient support surface into the flex and reflex positions.

Further, during many operations, the patient is reversed from the normal orientation on the table wherein the table is reconfigured with the head section moved to the foot end and mounted to the end of the leg section whereby the leg section supports the back of the patient and the back section supports the legs of the patient. In prior art tables, a controller is provided with a reverse button to accommodate the reverse position of the patient such that the direction of movement of the table will be reversed from the direction of movement provided in the normal mode of operation. For example, in the normal mode of operation, pushing the trendelenburg button will cause the table to move into a position with the head end down lower than the foot end, and in the reverse mode of operation, pushing the same button will cause the foot end of the table to be positioned lower than the head end whereby a patient oriented in the reverse position will have his or her head positioned downwardly. Similarly, pushing the reverse button on the prior art controller will cause the lateral tilt to be reversed wherein the left or right tilt of the patient will occur with reference to an operator standing adjacent to the head of the patient. Such a control system requires that the operator be aware of which end of the table is designated as the head end or foot end in order to properly determine whether the patient is in a normal or reverse position on the table. Thus, coordinating the controls for the table with the particular patient orientation requires an additional step on the part of the operator.

During certain surgical operations, it is desirable to move a portion of the patient wherein one section of the surgical table pivoted out of alignment with another adjacent section of the table is moved into a neutral position aligned parallel to the adjacent table section. For example, in an operation with the patient oriented in a reverse position with the back of the patient resting on the leg section of the table and the leg section pivoted upwardly from the seat section, it may be desirable to move the leg section downwardly into alignment with the seat section without altering the position of the seat section relative to a support member for supporting the table top. During a typical operation, this realignment of a portion of the table top is complicated by the provision of a draping extending over the patient and downwardly over the sides of the table such that the relative orientation of the table top sections cannot be readily observed without lifting the draping.

Accordingly, there is a need for an articulated surgical table having an actuator and control system which permits the table to be easily manipulated to desired positions while minimizing the level of operator input required.

SUMMARY OF THE INVENTION

The present invention provides a surgical table including an articulated table top which facilitates orientation of a patient for different surgical operations.

In one aspect of the invention, a surgical table is provided comprising a table top, a support for supporting the table top, an actuator for moving the table top relative to the support, and a controller having selectable functions for energizing the actuator to move the table top in a normal mode of operation when the surgical table is in a first configuration and having a reverse mode of operation for reversing the selectable functions in a second configuration of the surgical table.

In a further aspect of the invention, the table top comprises a plurality of sections for supporting a patient and movement of one of the sections relative to at least one other of the sections causes the surgical table to be reconfigured into the second configuration. Preferably, the plurality of sections includes a back section, a head section mountable to the back section in the first configuration, a seat section connected to the back section and a leg section connected to the seat section. The head section defines a moveable section for the table wherein the head section may be mounted to the leg section to reconfigure the surgical table for the second configuration thereof.

In a further aspect of the invention, the table is provided with sensors including switches associated with apertures located at first and second ends of the table top. The head section is provided with pins for engaging within the apertures wherein the pins are operable to actuate the switches whereby the controller is provided with a signal indicating the particular configuration for the surgical table.

In yet another aspect of the invention, a method for controlling articulation of a surgical table is provided including the steps of operating a controller to energize an actuator for moving a top portion of the table in accordance with preselected functions in a normal mode of operation, reconfiguring the surgical table to cause the controller to be automatically switched to a reverse mode of operation, and operating the controller to energize the actuator in the reverse mode of operation wherein the preselected functions are reversed from the normal mode of operation.

In a further aspect of the invention, a surgical table is provided comprising a table top, a support for supporting the table top, an actuator system for moving the table top relative to the support, a controller having selectable functions for energizing the actuator system to move the table top, and wherein the controller automatically deactivates the actuator system when a predetermined portion of the table top reaches a neutral position. The neutral position corresponds to positioning of a section of the table top in alignment substantially parallel to an adjacent section of the table top. In accordance with this aspect of the invention, a manually actuable switch is provided for activating at least one of the selectable functions for moving the predetermined portion of the table top to the neutral position. The switch further being operable for activating the selectable function for moving the predetermined portion of the table top away from the neutral position. The selectable functions include lateral left and right tilt functions, trendelenburg and reverse trendelenburg functions, and functions controlling movement of a seat section and leg section for the table.

In another aspect of the invention, a method for controlling articulation of a surgery table is provided including the steps of selecting a first function on a controller for energizing an actuator system to move a portion of a table top for the surgical table in a first direction, selecting a second function on the controller to energize the actuator system for moving the portion of the table top in a second direction opposite the first direction, and wherein the controller automatically terminates movement of the portion of the table top in the second direction when the portion of the table top reaches a neutral position. The method of controlling articulation of the surgical table further includes the step of disengaging the second switch and again engaging the second switch to continue movement of the portion of the table top past the neutral position in the second direction.

In yet a further aspect of the invention, a surgical table is provided comprising an articulated table top including a back section, a seat section and a leg section, the seat section being pivotably mounted relative to the back section; a support for supporting the table top; a system of actuators for moving the sections of the table top; a controller for energizing the system of actuators, the controller having a normal mode of operation and a reverse mode of operation; and the controller being operable to energize the system of actuators to configure the table in flex and reflex positions wherein a flex/reflex point in the normal mode of operation is located between the back and the seat sections, and a flex/reflex point in the reverse mode of operation is located between the seat and the leg sections.

In another aspect of the invention, a support cushion is provided for use with the surgical table wherein the support cushion includes an upper layer defined by a foam cushion and a lower layer defined by a flexible x-ray transparent sheet of material, the lower layer being sufficiently rigid to form a support for continuously supporting the weight of a patient across a gap between adjacent sections of the table. The lower layer is preferably formed of polypropylene and is adapted to provide a continuous bridge across the gap during a flex movement of the surgical table.

In another aspect of the invention, a surgical table is provided comprising a table top including at least a seat section and a leg section mounted to the seat section; a support for supporting the table top; an actuator for driving the leg section in pivotable movement relative to the seat section from a raised position approximately 80° above a plane defined by the seat section to a lowered position approximately 105° below the plane; and wherein a force applied to the leg section during the pivotable movement varies and the force is a maximum when the leg section is at the raised position.

Therefore, it is an object of the present invention to provide a surgical table including a controller wherein control of the surgical table by an operator is facilitated.

It is a further object of the invention to provide such a surgical table wherein the surgical table automatically accommodates reverse positioning of a patient.

Other objects and advantages of the invention will be apparent from the following description, the accompanying drawings and the appended claims.

BRIEF DESCRIPTION OF THE DRAWINGS

FIG. 2 is a diagrammatic plan view of the surgical table;

FIG. 3 is a side elevational diagrammatic view of the surgical table in a trendelenburg position;

FIG. 4 is a side elevational diagrammatic view of the surgical table in a reverse trendelenburg position;

FIG. 5 is an end view diagrammatically showing a left lateral tilt of the surgical table;

FIG. 6 is an end view diagrammatically showing a right lateral tilt for the surgical table;

FIG. 7 is a side elevational diagrammatic view illustrating seat up and seat down positions;

FIG. 8 is a side elevational diagrammatic view illustrating the maximum raised and lowered positions for the leg section;

FIG. 9 is a side elevational diagrammatic view illustrating a flex position;

FIG. 10 is a side elevational diagrammatic view illustrating a reflex position;

FIG. 11 is a top plan view illustrating a head section for the surgical table;

FIG. 12 is an end view of the pin end of the head section;

FIG. 13 is an end view of the pin end of the leg section;

FIG. 14 is an end view of the seat section showing the mounting points for the leg section;

FIG. 15 is a side elevational diagrammatic view illustrating the surgical table in a flex position during a reverse mode of operation;

FIG. 16 is a side elevational diagrammatic view illustrating the surgical table in a reflex position during a reverse mode of operation;

FIG. 17 is a perspective view, partially cut away, of a patient support cushion for use with the present surgical table;

FIG. 18 is a cross-sectional end view through the patient cushion of FIG. 17;

FIG. 29 is a perspective view of a side extender assembly for the surgical table mounted to the table;

FIG. 30 is an exploded view of the side extender assembly of FIG. 29;

FIG. 31 is a side elevational view showing two side extender assemblies mounted to a portion of the surgical table; and FIG. 32 is an end view of the side extender assembly mounted to a portion of the surgical table.

DETAILED DESCRIPTION OF THE PREFERRED EMBODIMENT

Figure 1:
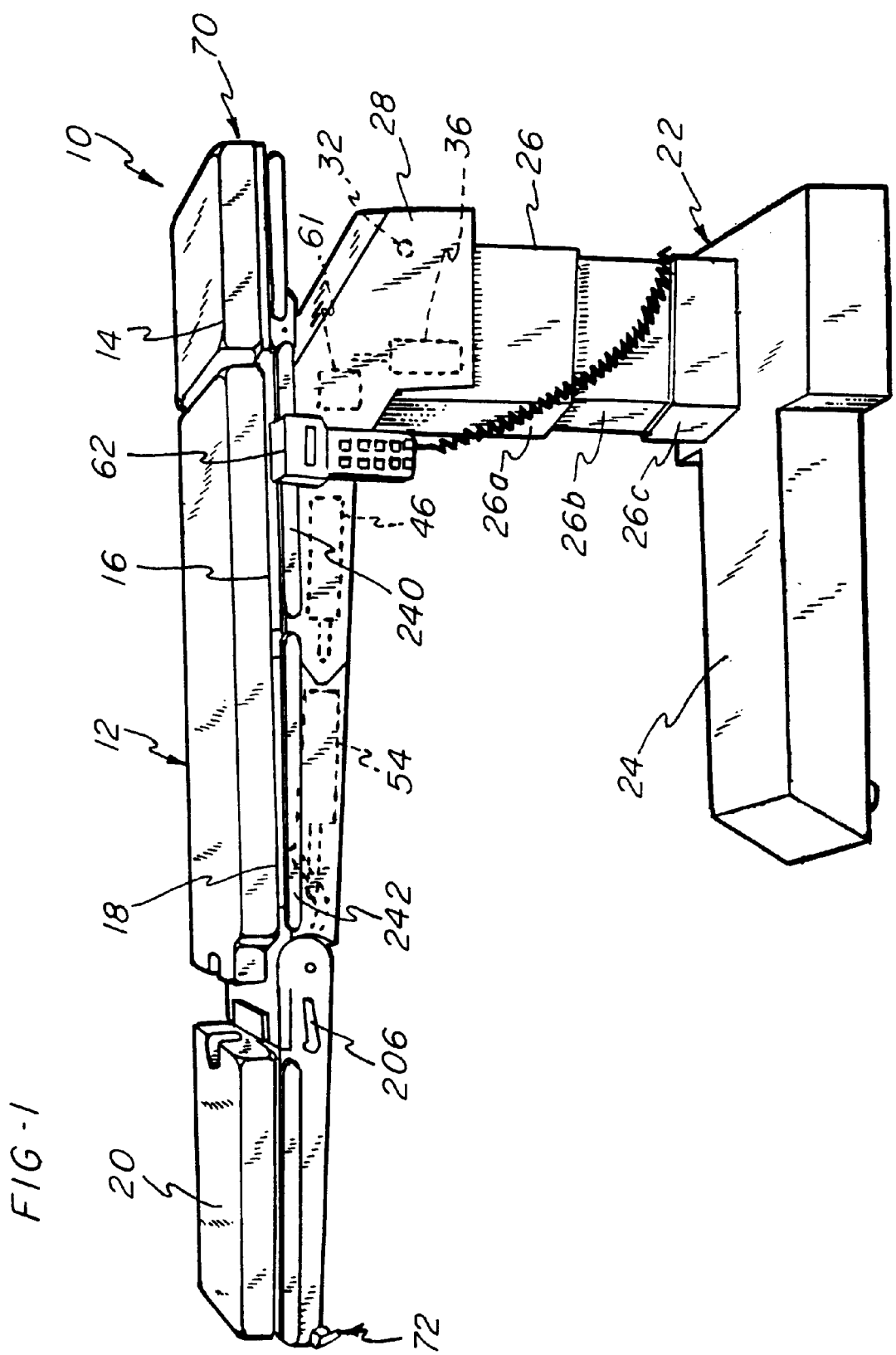
FIG. 1 is a perspective view of the surgical table of the present invention.

Referring to FIGS. 1 and 2, the surgical table 10 of the present invention comprises a table top 12 formed of a plurality of interconnected articulated sections including a head section 14, a back section 16, a seat section 18 and a leg section 20. The table top 12 is supported on a support 22 including a base 24, a support column 26 extending upwardly from the base 24 and a support bridge 28 mounted to the top of the support column 26 and rigidly supporting the back section 16 of the table top 12.

The support column 26 is vertically extendable and includes telescoping sections 26a, 26b and 26c for providing upward and downward movement of the table top 12. The mechanism for providing the upward and downward movement of the support column 26 is conventional and known in the art.

The support bridge 28 is supported on the top of the column 26 for movement about a lateral tilt axis 30 and a longitudinal tilt axis 32 (see FIG. 2). The bridge 28 is actuated for movement relative to the support column 26 by means of an actuator 34 causing the bridge and table top 12 to undergo lateral tilt movement about the axis 30, and an actuator 36 for causing the bridge 28 and table top 12 to undergo longitudinal tilt movement, such as for trendelenburg positions, about the axis 32. The actuation mechanism for moving the bridge 28 relative to the column 26 is shown diagrammatically for illustrative purposes only and may comprise any known mechanism for tilting a surgical table about two axes. For example, a mechanism similar to that disclosed in U.S. Pat. No. 4,148,472 to Rais, et al., incorporated herein by reference, may be satisfactory for use in the present surgical table.

The table top sections 14, 16, 18, 20 each include a frame supporting a support plate, and a cushion is attached to the upper surface of the support plate to provide a cushioned surface for a patient. Further, the table 10 is also designed as a cantilever structure with the back section 16, seat section 18 and leg section 20 extending in laterally spaced relation relative to the support column 26 to provide maximum clearance for performing x-ray procedures. Also, the section frame portions, including the back section engaging portions of the bridge 28, are located adjacent to the lateral edges of the table sections such that the central portions of the table sections are clear of obstruction, such as metal frame members, for facilitating performing x-ray procedures.

As best seen in FIG. 2, the head section 14 is removably mounted to one end of the back section 16 at pin mounting points 38 and 40. The seat section 18 is pivotably connected to the other end of the back section 16 at articulated pivot connection points 42 and 44. Actuators in the form of power cylinders 46 and 48 are mounted within the side frame portions of the back section 16 for actuating the seat section 18 in pivotable movement upwardly or downwardly relative to the back section 16. The leg section 20 is removably mounted to the seat section 18 at pin mounting points 50 and 52 comprising pivotably mounted blocks which are actuated for movement by leg actuator mechanisms 54 and 56. The leg actuator mechanisms 54 and 56 will be described in greater detail below.

It should be noted that a gap 58 is defined between the back section 16 and the seat section 18, and a further gap 60 including a perineal cutout is provided between the seat section 18 and the leg section 20. The gaps 58 and 60 are adapted to provide sufficient space for a kidney riser to be incorporated into the table when necessary for particular operations.

The surgical table 10 is provided with a pre-programmed controller including a microprocessor 61 and a hand held pendant controller 62 (see FIGS. 1, 3 and 20) for controlling movement of the table 10. In addition, as depicted in FIG. 3, a further controller or control panel 63 similar to pendant controller 62 may be provided permanently mounted to a side of the table 10 wherein the control panel 63 is adapted to control the table 10 independently of the microprocessor 63. The programmed controller 61 is programmed to provide various selected functions for the table 10, which functions may be selected by pressing different buttons on a panel 64 of the pendant or panel mounted controllers 62, 63. For example, the control system may be turned on and floor locks (not shown) mounted within the base 24 may be actuated by pressing button 66 (FIG. 20) on the panel 64 whereby the locks move into position in engagement with a floor or surface. The floor lock mechanism described in U.S. patent application No. (Attorney Docket No. MID 173 P2), assigned to the assignee of the present invention, may be used in conjunction with the present table, and the disclosure of this U.S. patent application is incorporated herein by reference.

Figure 22:
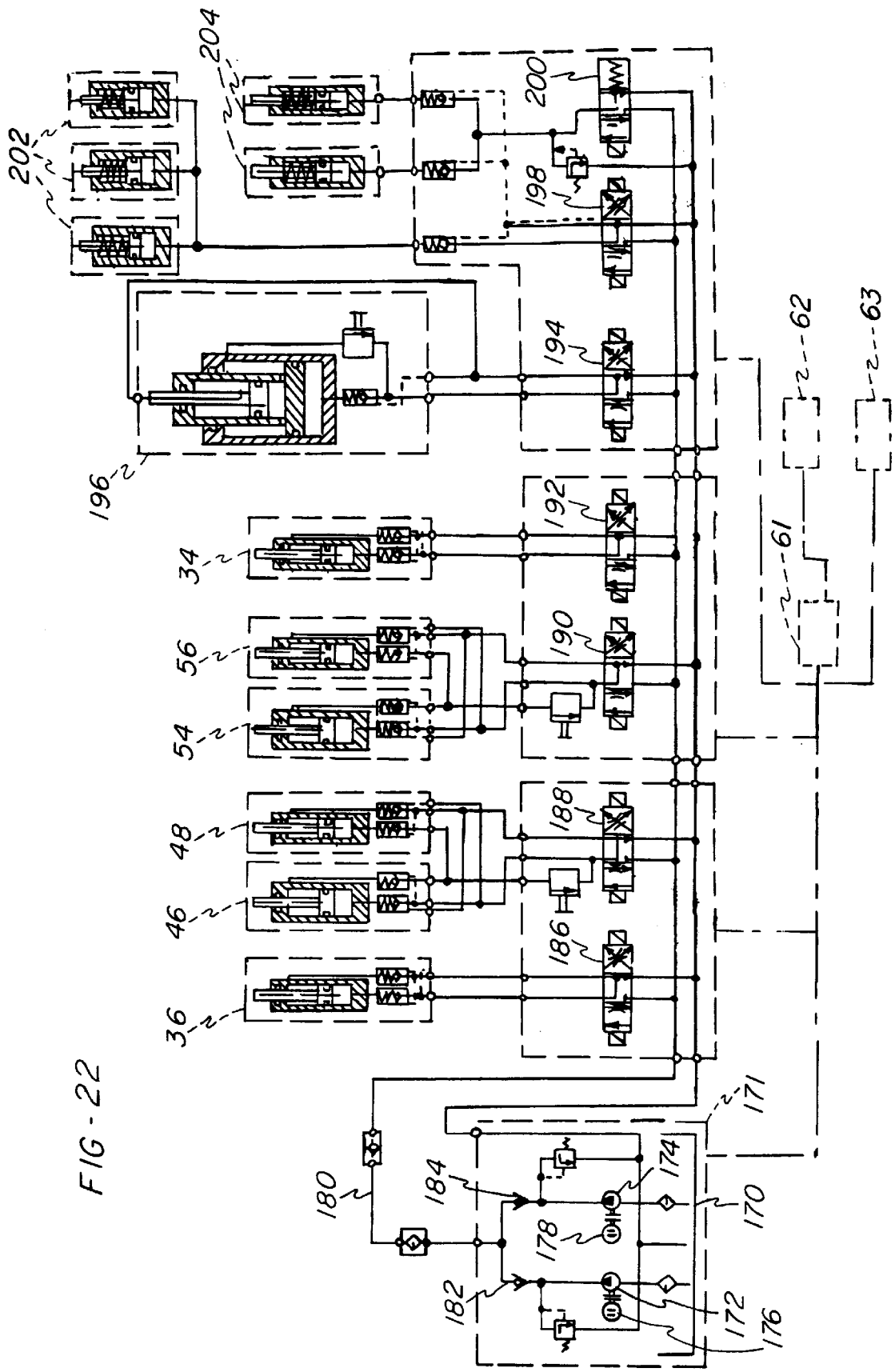
FIG. 22 is a hydraulic diagram illustrating the hydraulic system for use in the present invention.

Referring to FIG. 22, a hydraulic system for the present surgical table 10 is illustrated diagrammatically. It should be understood that the controllers 62, 63 are each operable to control actuation of the hydraulic system in order to actuate the various portions of the table 10 for movement. The hydraulic system includes a pump system 171 comprising an oil reservoir 170 within which is located a first pump 172 and a second pump 174 driven by respective first and second motors 176, 178 preferably located outside of the oil reservoir 170. One of the pumps, for example the first pump 172, is the main pump for the surgical table 10, and the other pump, for example the second pump 174, is a backup pump for use if the main pump 172 should become inoperable. The pumps 172, 174 are connected to a common output line 180 through respective check valves 182, 184. The output line 180 defines a pressurized fluid supply for the various actuation cylinders used in the surgical table 10, and a return line 180 is provided for returning oil to the reservoir 170.

In addition, control valves are provided for controlling the fluid flow through the hydraulic system. Specifically, control valve 186 is provided for controlling the bridge tilting actuator 36, control valve 188 is provided for controlling actuators 46 and 48 for moving the seat section 18, control valve 190 is provided for controlling actuation of the leg actuator mechanisms 54 and 56, control valve 192 is provided for controlling actuation of the lateral tilt actuator 34, control valve 194 is provided for controlling an actuator 196 for providing a vertical height adjustment for the table and control valves 198, 200 are provided for controlling actuation of floor lock actuators 202 and 204, as is described further in the above-noted U.S. patent application No. (Attorney Docket No. MID 173 P2).

It should be noted that either of the controllers 62, 63 may be used to energize the pump system 171 and the control valves 186, 188, 190, 192, 194, 198, 200. Generally, the movements of the surgical table 10 will be controlled by the pendant controller 62 operating the main pump, for example the first pump 172. However, in the event that the pump 172 should fail in some manner, the backup pump, for example second pump 174, is available to run the system. It should be noted that the system is configured such that when the main pump 172 becomes inoperable, the pendant controller 62 is disabled to control the surgical table 10, such that an operator must use the control panel 63 mounted to the table 10 in order to actuate the table for movement. Further, use of the controller 63 results in the second pump 174 being energized to provide pressurized fluid to the hydraulic system. This arrangement ensures that the operator is aware of a malfunction in the pump system, as indicated by the pendant controller 62 being rendered inoperable, such that repairs will be effected in a timely manner to the malfunctioning pump to ensure that both pumps are operational.

FIGS. 3–10 illustrate various movements provided for the surgical table 10 by the controllers 62 and 63 wherein the support plate and frame portions of the table top sections are illustrated diagrammatically to show the different positions. The positions provided by the controllers 62, 63 will be described with particular reference to the pendant controller 62 (see FIG. 20) and are as follows: button 68 provides a trendelenburg position, as shown in FIG. 3, with a head end 70 of the table located lower than a foot end 72 of the table; button 74 provides a reverse trendelenburg position, as illustrated in FIG. 4; buttons 76 and 78 control the support column 26 to provide raised and lowered positions, respectively, of the table top 12; buttons 80 and 82 provide left and right lateral tilt, as viewed from the head end 70 and illustrated in FIGS. 5 and 6, respectively; button 84 functions to move the seat section 18 upwardly, as illustrated in solid lines in FIG. 7; button 86 functions to move the seat section downwardly, as illustrated in dotted lines in FIG. 7; buttons 88 and 90 function to provide leg up and leg down functions, as illustrated in FIG. 8 by solid and dotted lines, respectively; button 92 functions to provide a flex position for the table, as illustrated in FIG. 9; button 94 functions to provide a reflex position for the table, as illustrated in FIG. 10; and button 96 functions to move all of the table top sections to a level position. In addition, an unlock button 98 is provided wherein simultaneously pressing the button 98 and the button 66 causes the floor locks to disengage from the floor, and a button 100 is provided for switching the table off after table positioning is completed, although the table will normally automatically be disabled ten seconds after the last button on the pendant controller 62 is depressed. When the table has been turned off, it is necessary to first press the enable button 66 before proceeding with a positioning operation.

Referring to FIG. 11, the head section 14 is illustrated removed from the table 10 and includes side rails 102, 104 for mounting accessories. The head section 14 also includes mounting pins 106 and 108 for mounting the head section 14 to the pin mounting points 38 and 40 located on the back section 16 as well as to pin mounting points 50, 52 on the seat section 18 and to pin mounting points 110 and 112 provided at the end of the leg section 20, as shown in FIG. 2.

Referring to FIG. 12, an end view of the head section 14 is shown wherein the pin 108 includes a flattened portion 114. Similarly, as seen in FIG. 13, the leg section 20 includes mounting pins 116 and 118 wherein the pin 116 includes a flattened portion 120. It should be noted that the pin 108 having the flattened portion 114 on the head section 14 is located on an opposite side from the side of the leg section 20 having the pin 116 with a flattened portion 120.

Referring to FIG. 14, the end of the seat section 18 for receiving mounting pins of either the head section 14 or the leg section 20 is shown and includes mounting pin apertures 122 and 124. Associated with each of the apertures 122 and 124 are respective sensors or sensor switches 126 and 128. The switches 126 and 128 each include a respective plunger 130 and 132 for extending into the apertures 122 and 124. Thus, if the head section 14 is attached to the seat section 18 with the pins 106 and 108 extending into the apertures 122 and 124, respectively, the pin 106 will actuate the switch 126 while the flat portion 114 of the pin 108 will cause the switch 128 to remain unactuated. This will signal the controller 61 for the surgical table 10 that the head section 14 is attached to the table at this particular location.

Alternatively, when the leg section 20 is attached to the seat section 18, the switch 128 is actuated while the switch 126 remains unactuated to signal the controller 61 that the leg section 20 is in position at this particular location adjacent to the seat section 18. Similar switches are provided at the pin mounting points 38 and 40 of the back section 16, as well as at the mounting point 110 at the end of the leg section 20. Further, the seat section mounting points 50 and 52 include electrical connectors 134 and 136, respectively, extending from the controller 61 and adapted to engage connectors (not shown) on a section attached to the seat section, such as on the leg section 20, whereby electrical connections to a switch or switches associated with mounting points at a distal end of the attached section are provided.

It should be noted that the above description of the different movements of the surgical table 10 in response to actuation of the buttons on the pendant controller 62 was made with reference to a normal mode of operation wherein the head section 14 was connected to the back section 16 such that the patient's head is positioned adjacent to the head end 70 of the table 10. In a reverse mode of operation, the head section 14 would be positioned with the pins 106 and 108 engaged within the pin mounting points 110 and 112, respectively, of the leg section 20, or within the mounting points 50, 52 of the seat section 18. A switch associated with the mounting point 110 or 50 and 52 would signal the controller 61 that the head section 14 is mounted at the foot end of the table. In response to this signal, the controller will automatically reverse the control movements for the table. For example, with the head section 14 attached to the end of the leg section 20, pressing the trendelenburg button 68 will cause the foot end of the table 72 to lower to a position below that of the head end 70, and a reverse movement will occur when the reverse trendelenburg button 74 is depressed. Similarly, pressing the left lateral tilt button 80 will cause the table to tilt to the left as viewed from the foot end 72 of the table, and an opposite movement will occur in response to depressing the right lateral tilt button 82. Similarly, a relocation of the articulation points for flex/reflex movements will occur, as is described further below.

In addition, it should be noted that certain procedures may require that the leg section 20 be attached to the mounting points, 38, 40 on the back section 16 and the head section 14 be attached to the mounting points 50, 52 on the seat section 18. The controller 61 is adapted to sense the particular locations of the leg and head sections 20 and 14 via the system of sensors and reverse the control operations accordingly.

It should be noted that when the patient is reversed on the table, the patient's back will then rest upon the leg section 20, the patient's buttocks will rest on the seat section 18 and the patient's lees will rest on the back section 16. For the purpose of clarity, in the reverse mode of operation the back section 16 and leg section 20 will be referenced with the same terminology as used with the patient in the normal position, although the portions of the patient supported by the sections in the reverse mode of operation are reversed.

Figure 20:
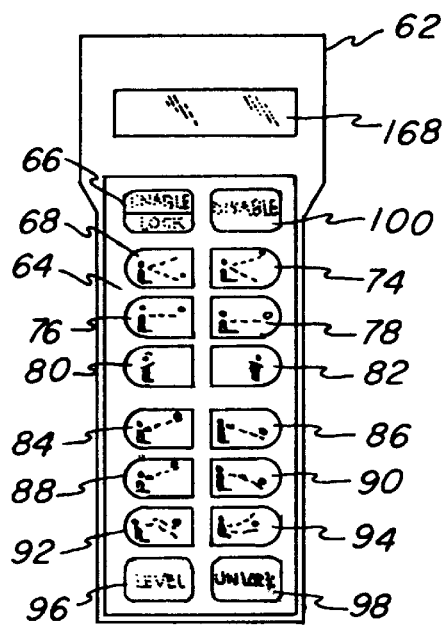
FIG. 20 is a front view of a pendant controller for the surgical table.

As seen in FIG. 20, the buttons on the pendant controller 62 are provided with diagrammatic illustrations showing the movement resulting from depressing the particular button. The movement of the table in the normal mode of operation is illustrated with a solid circle showing the location of the patient's head, and the movement of the table in the reverse mode of operation is illustrated showing the location of the patient's head with an outline circle. Thus, it can be seen from the illustrations on the controller buttons that the various movements for each of the selected functions are reversed from the normal mode of operation when the head section is moved to the foot end of the table.

Referring to FIGS. 15 and 16, the flex and reflex movements of the table are illustrated with the table operating in the reverse mode of operation. In addition, support cushions 138, 140 and 142 are shown positioned on top of the table top sections 16, 18, 20 and 14. It should be noted that the flexure point 144 for the flex/reflex function of the table in the reverse mode of operation is displaced from the flexure point 146 for the flex/reflex function of the surgery table in the normal mode of operation, as seen in FIGS. 9 and 10. Specifically, in the normal mode of operation, the flexure point 146 is located between the back section 16 and the seat section 18, whereas in the reverse mode of operation, the flexure point 144 is located between the seat section 18 and the leg section 20. This shift in the flexure point occurs automatically in response to the change in the mounting point of the head section 14 from the head end 70 of the table to the foot end 72 of the table. This shift in the flexure point is necessary since the patient's hip will be moved from the flexure point 146 to the flexure point 144 when the patient is reversed on the table, and the table is reconfigured to accommodate the patient in this position.

Figure 23:
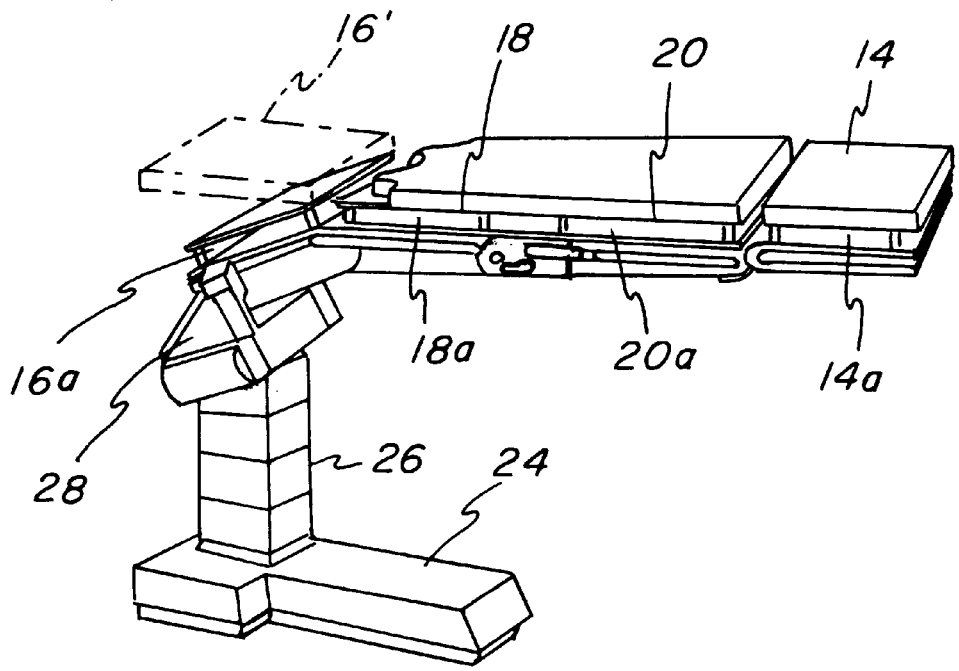
FIG. 23 is a perspective view showing the surgical table in an extreme elevated position.
Figure 24:
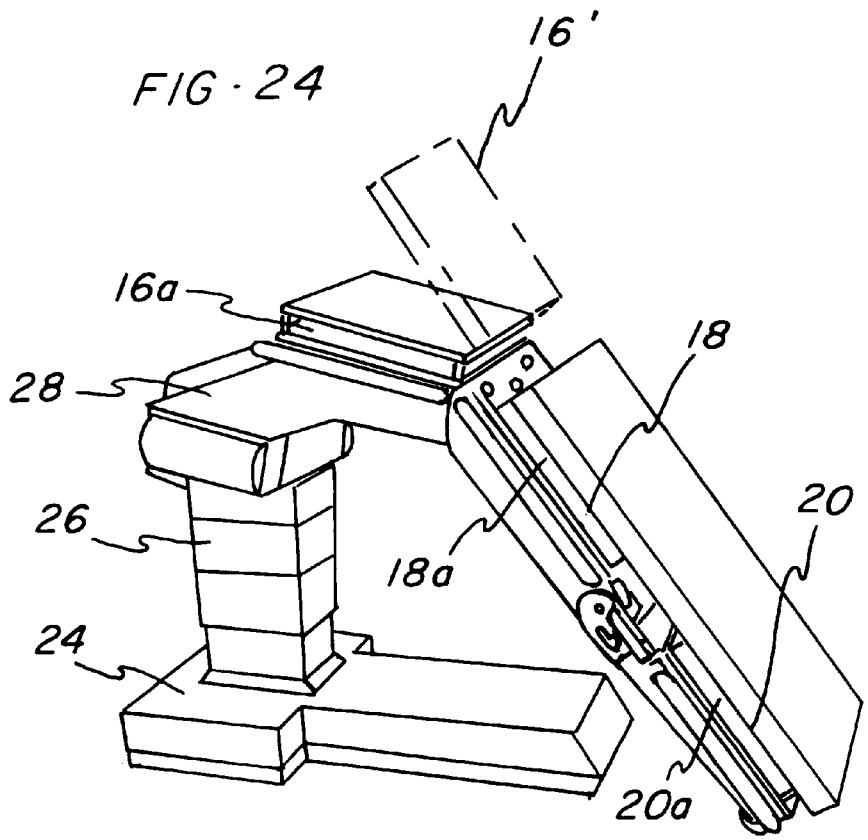
FIG. 24 is a perspective view showing the surgical table in an extreme trendelenburg position.

Referring to FIGS. 23 and 24, it can be seen that the present table is adapted to provide extreme positions for positioning a patient which are not typically available with prior art surgical tables. Specifically, FIG. 23 shows a position of the present surgical table 10 wherein the table 10 is configured in the reverse configuration with the bridge 28 pivoted upwardly and the back section 18, leg section 20 and head section 14 are oriented substantially parallel to the floor and tilted laterally to one side. Further, an additional patient support section 16' may be attached to an end of the back section 18 and extending outwardly over the seat section 16 to provide further support for the patient. In this orientation of the table, a patient will be placed on the table in a reverse position at an increased height over that of the normal level position shown in FIG. 1. This position facilitates chest surgery, for example, wherein a surgeon may stand behind the table (as seen in FIG. 23) with the patient at approximately chest height relative to the surgeon.

Referring to FIG. 24, the table 10 is shown in an extreme trendelenburg position with the bridge 28 tilted downwardly to increase the vertical orientation of the table top 12. In this configuration, the additional patient support section 16' described above with regard to FIG. 23 may also be added to the end of the back section 18 in order to provide a further patient support surface. This position for the table may prove important for surgical procedures involving obese patients wherein the additional movement of the table top toward a vertical position facilitates the use of gravity to draw the organs of the patient in a desired direction. Thus, it should be apparent from FIGS. 23 and 24 that the present invention enables an operator to obtain extreme positions, such as extreme height or extreme vertical orientation, for positioning a patient. Further, it should be noted that the cantilever construction of the present table facilitates obtaining such extreme positions.

Referring to FIGS. 17 and 18, the cushion 140 for supporting the patient is further illustrated and includes structure for continuously supporting the patient over the gaps which occur between adjacent sections of the table, for example the gaps located at 58 and 60. The cushion 140 is preferably designed to extend over two sections of the table and is formed with a soft foam upper layer 148 and a flexible lower layer 150 which is sufficiently rigid to form a support for continuously supporting the weight of a patient across a gap 58, 60 located between adjacent sections of the table. The lower layer is preferably formed from an x-ray transparent sheet of material such as polypropylene. Further, the lower layer of polypropylene is preferably formed with a thickness of approximately 2 mm such that the polypropylene layer is flexible while also sufficiently rigid to form a bridge supporting a patient across the gap in the table. The upper layer 148 and lower layer 150 are surrounded by an outer cover 152 wherein the outer layer 152 is formed of an upholstery material, such as vinyl. As can be seen in FIGS. 15 and 16, the provision of such a cushion is particularly useful for providing a smooth continuous surface between table sections during flexure of the table top 12.

Figure 19:
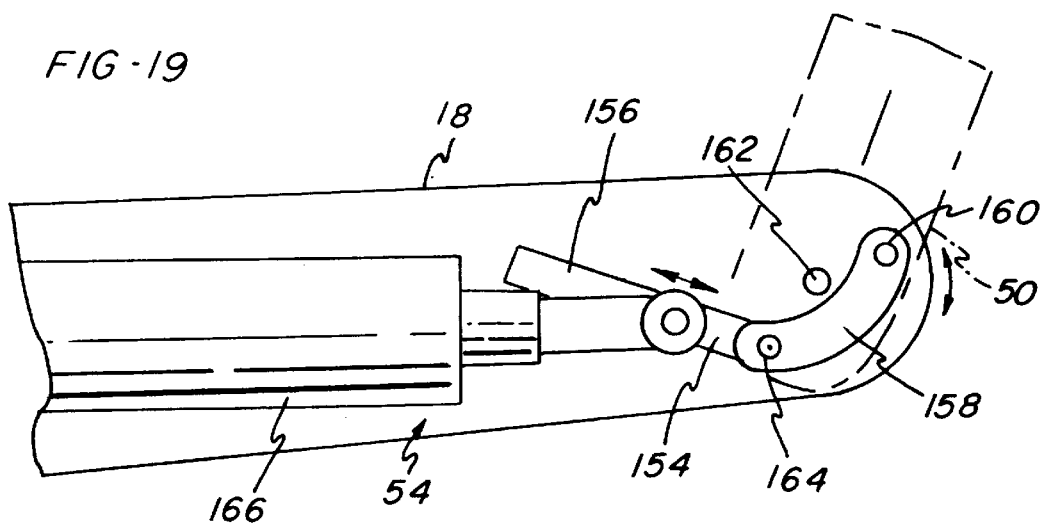
FIG. 19 is a side elevational diagrammatic view illustrating one of the actuation mechanisms for the leg section of the surgical table.

Referring to FIGS. 8 and 19, the leg section 20 of the present table is adapted to move between a raised position of 80° above a plane defined by the seat section 18 to a lowered position 105° below the plane defined by the seat section 18. The raised position is typically used in the reverse mode of operation for supporting a patient substantially upright relative to the seat section 18, and the lowered position is typically used to move the leg section 20 out of the way during a normal mode of operation procedure such as one wherein access near the perineal cutout area of the table is required. During such movement of the leg section 20 it has been found that it is desirable to have the greatest available torque or force available for moving the leg section 20 when the leg section 20 is adjacent to its uppermost position, and the least force is required when the leg section is in its lowered position. Accordingly, the actuation mechanism 54 illustrated in FIG. 19 (which is identical to the actuation mechanism 56) is designed to provide a maximum force when the leg section 20 is in its raised position and to provide the least force when the leg section 20 is in the lowered position.

The actuation mechanism 54 includes a slide 154 mounted for sliding movement between a pair of facing slots 156 (one of which is shown) formed in the frame for the seat section 18. A linkage 158 is provided and includes a first end 160 connected to the mounting point block 50 for connection to the leg section 20. It should be noted that the mounting point 50 is defined as a block pivotably mounted to the seat section 18 a pivot point 162. The linkage 158 includes a second end 164 connected to the slide 154. It should be noted that the first and second ends 160 and 164 of the linkage 158 are pivotal at their connections with the mounting point block 50 and the slide 154, respectively. The slots 156 define a linear path for the slide 154 wherein the path defined by the slots 156 advantageously extends downwardly in a direction toward the leg section 20. A driver in the form of a power cylinder, such as a fluid cylinder 166 is connected to the slide 154 for driving the slide 154 along the path defined by the slots 156. It has been found that by providing the particular drive connection illustrated in FIG. 19, that a maximum force is obtained when the leg section 20 is in its upper position and a minimum force is provided when it is in its lowered position such that an optimum compromise of varying forces during the movement of the leg section 20 is obtained.

In addition, it should be noted that the leg section 20 is formed as a unitary section such that the actuation mechanisms 54, 56 will cooperate to move the leg section 20. Further, to ensure that the force applied to the leg section 20 is distributed uniformly between the mechanisms 54 and 56, the fluid inlet side for one of the cylinders 166 for the mechanisms 54, 56 is in fluid communication with the fluid outlet of the other cylinder 166, and vice-versa, as may be seen in FIG. 22. Thus, the fluid pressure driving the cylinders 166 is equalized between the two actuation mechanisms 54 and 56.

Figure 21:
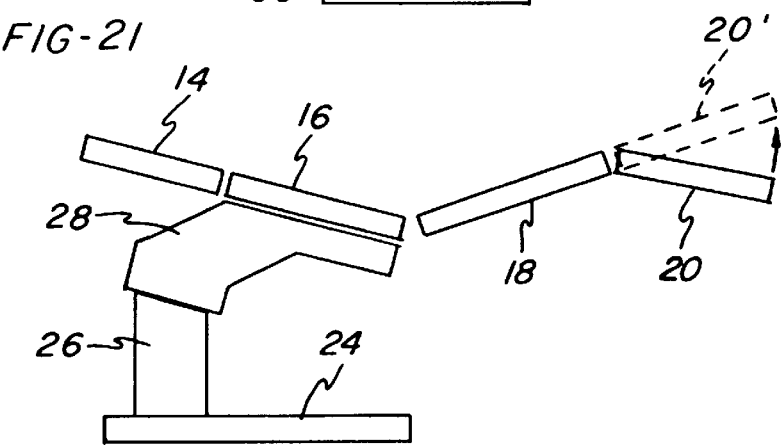
FIG. 21 is a side elevational diagrammatic view illustrating a return to neutral function of the surgical table.

Referring to FIGS. 20 and 21, the controller 61 for the present surgical table provides a further function which facilitates operator control of the table. During movement of any table section from a position out of alignment with an adjacent section back toward parallel alignment with the adjacent section, the controller 61 will cause the moving section to automatically stop at a neutral position wherein the two sections are aligned parallel to each other. For example, as illustrated in FIG. 21, as the leg section 20 is moved upwardly in response to depressing the button 88 of the controller 62, the leg section 20 will move upwardly as long as the button 88 is depressed, but only until it reaches the position shown in dotted lines and designated 20'. When the leg section 20 reaches the position 20', the controller will automatically terminate actuation of the actuator mechanisms 54 and 56. Movement of the leg section 20 may be continued by releasing and again depressing the button 88. The means for monitoring the position of the different sections may be provided in any conventional manner. For example, proximity sensors may be located on the cylinders for moving the different section, or separate sensors for sensing the relative position of the sections may be provided.

This return to neutral function provided by the controller 61 is considered to be an important feature for use in procedures wherein the operator must move the surgical table top to a position where two adjacent sections are aligned parallel to each other and wherein it is difficult to observe the parallel alignment of the table sections because of surgical draping extending downwardly along the sides of the table. Further, besides providing this function for the different articulated adjacent sections of the table, this function is also provided for the lateral tilt function wherein movement of the table in the lateral direction is terminated when the table reaches its level position in a lateral direction, and movement may be continued by releasing and re-depressing the lateral tilt button.

In addition, it should be noted that the return to neutral position described above with reference to FIG. 21 is different from the function provided by the level button 96 in that the level button 96 returns all of the sections to a position where they are planer to each other and level relative to the base. In the return to neutral function, the sections are not necessarily moved to a level position, except for in the lateral tilt direction, and individual sections may be moved into alignment with adjacent sections without altering the positioning of the adjacent section.

The hand pendant controller 62 is provided with a display 168 whereby information relating to the status of the table may be relayed to the operator. The display 168 is an LCD display and may provide information such as the mode of operation (normal/reverse), table function selected, status of the battery charge for powering the table and error messages which facilitate trouble shooting problems with the control system for the table.

Referring to FIGS. 25–28, a particular latching mechanism for attaching the leg section 20 to the seat section 18 is shown, and in particular an elevational cross-sectional view is shown through the aperture 122. Further, the latching mechanism is illustrated with reference to the pin 106 being inserted into and captured within the aperture 122.

The latching mechanism includes a lever, depicted in phantom lines as element 206 which is rotatably mounted to the side of the surgical table 10. The lever 206 includes an oval cam member 208 which is eccentrically located relative to a center of rotation for the lever 206. The cam 208 is engaged with a plunger assembly 210 having an upper shelf 212, a lower shelf 214, and a recessed area 216 defined between the upper and lower shelves 212, 214 and into which the cam 208 extends. The lower shelf 214 is defined on a lower portion 218 of the plunger assembly 210 and a coil compression spring 220 engages the lower portion 218 to provide an upward biasing force against the plunger assembly 210. Similarly, the upper shelf 212 is defined on an upper portion 222 of the plunger assembly 210 and is engaged by a spring 224 which is smaller than and exerts a lesser force than the spring 220.

The plunger assembly 210 further includes a latch pin 226 movable within and extending through an upper wall 228 of the upper portion 222. The latch pin 226 is biased upwardly within the plunger assembly 210 by a belleville washer spring 230. In addition, the latch pin 226 is guided in its vertical movement through the upper portion 222 by a guide shank 232 extending upwardly through the upper portion 222.

Figure 25:
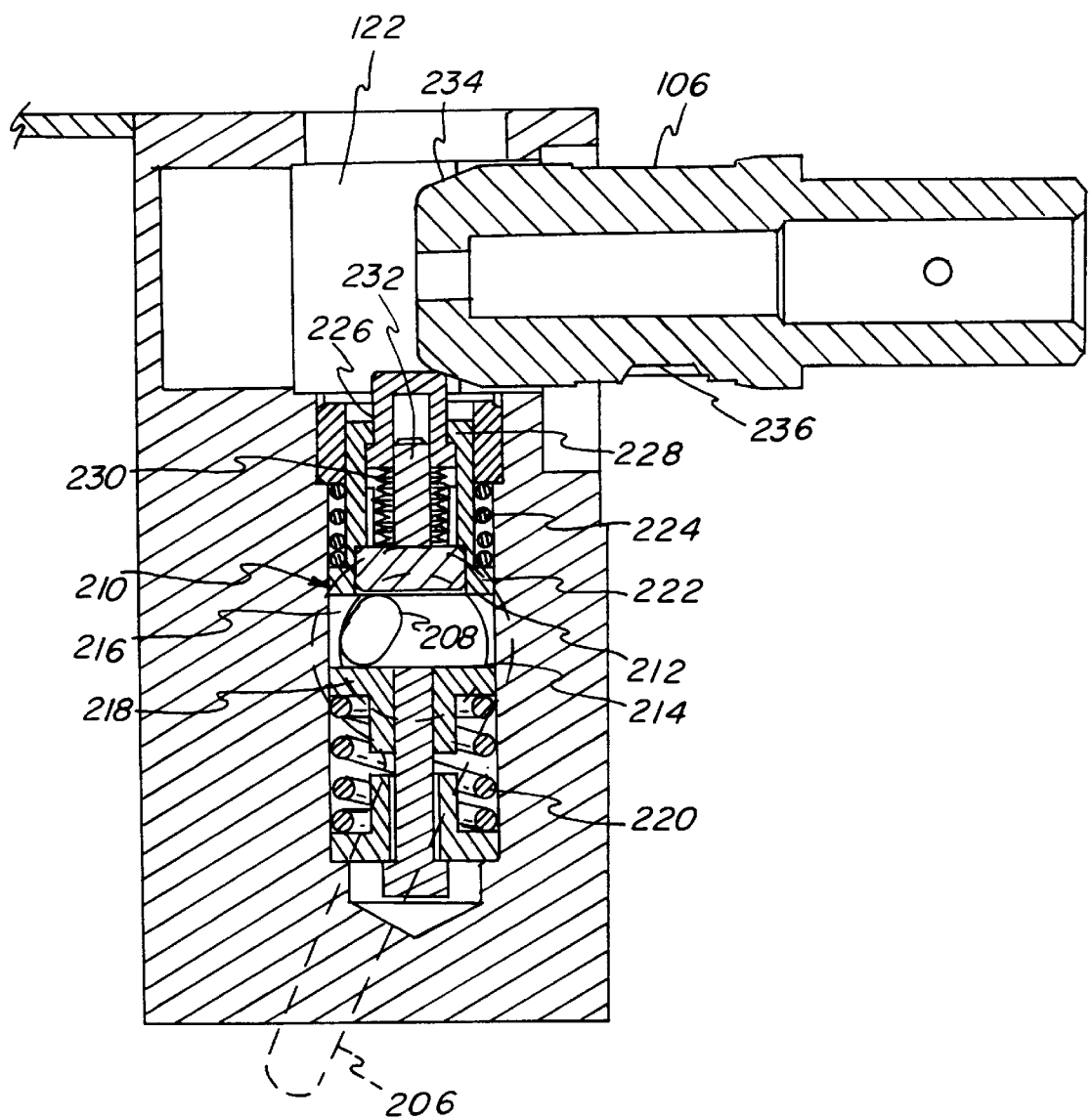
FIGS. 25–28 are cross-sectional elevational views illustrating a latching mechanism for latching the leg section to the seat section.
Figure 26:
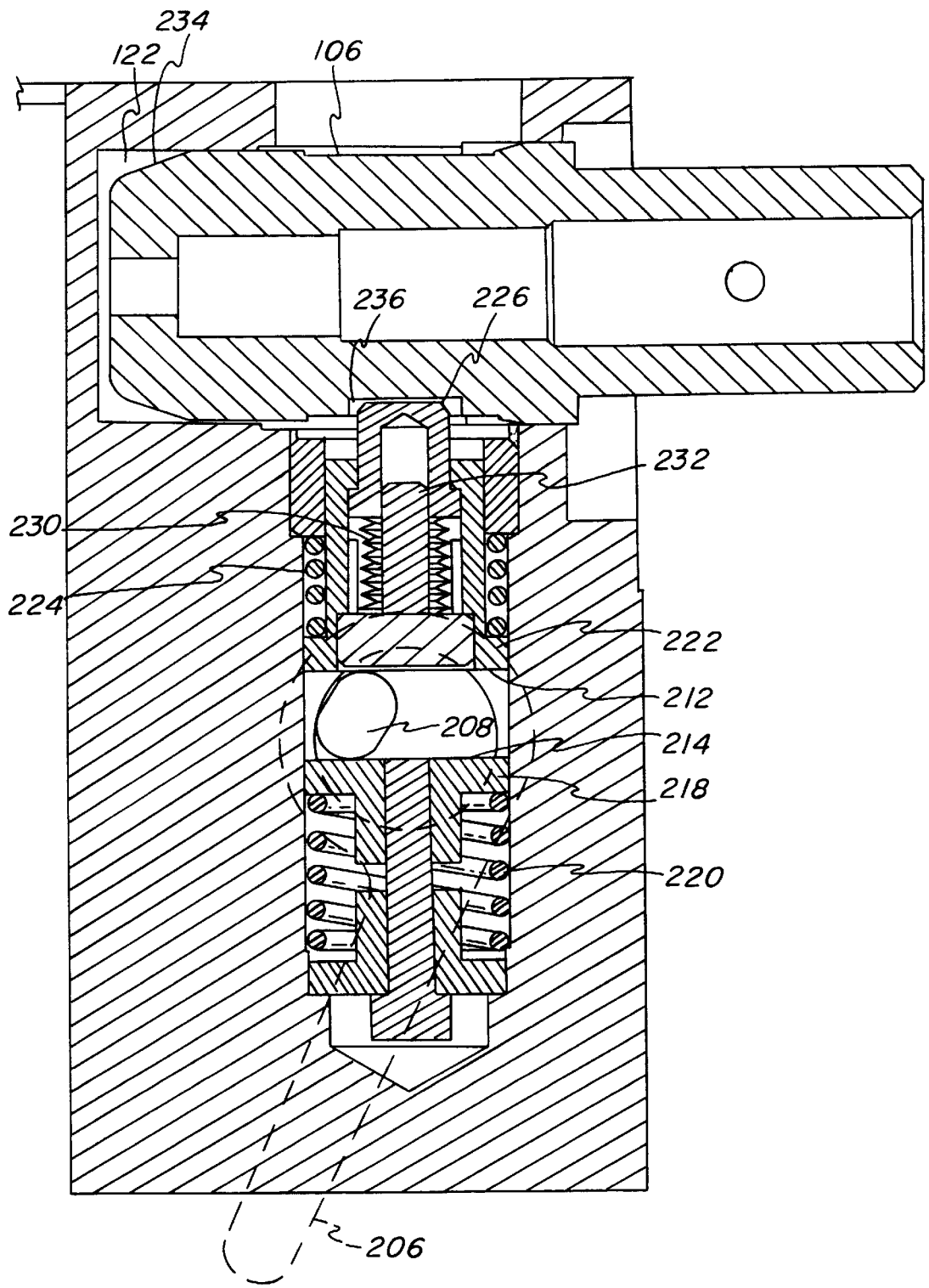

As seen in FIG. 25, the latch pin 226 normally extends upwardly into the aperture 122 and the pin 106 includes a blunt nose portion 234 for camming the latch pin 226 downwardly as the pin 106 is inserted into the aperture 122. As the latch pin 226 is cammed downwardly by the pin 106, the spring 220 will compress to permit downward movement of the plunger assembly 210. The pin 106 includes a slot 236 for receiving the latch pin 226 when the pin 106 is located in an engaged position within the aperture 122, as seen in FIG. 26. Thus, it should be apparent that the latching mechanism of the present invention provides for automatic latching of the pin 106 within the aperture 122 as it is inserted therein to thereby prevent removal of the pin 106 from the aperture 122.

Figure 27:
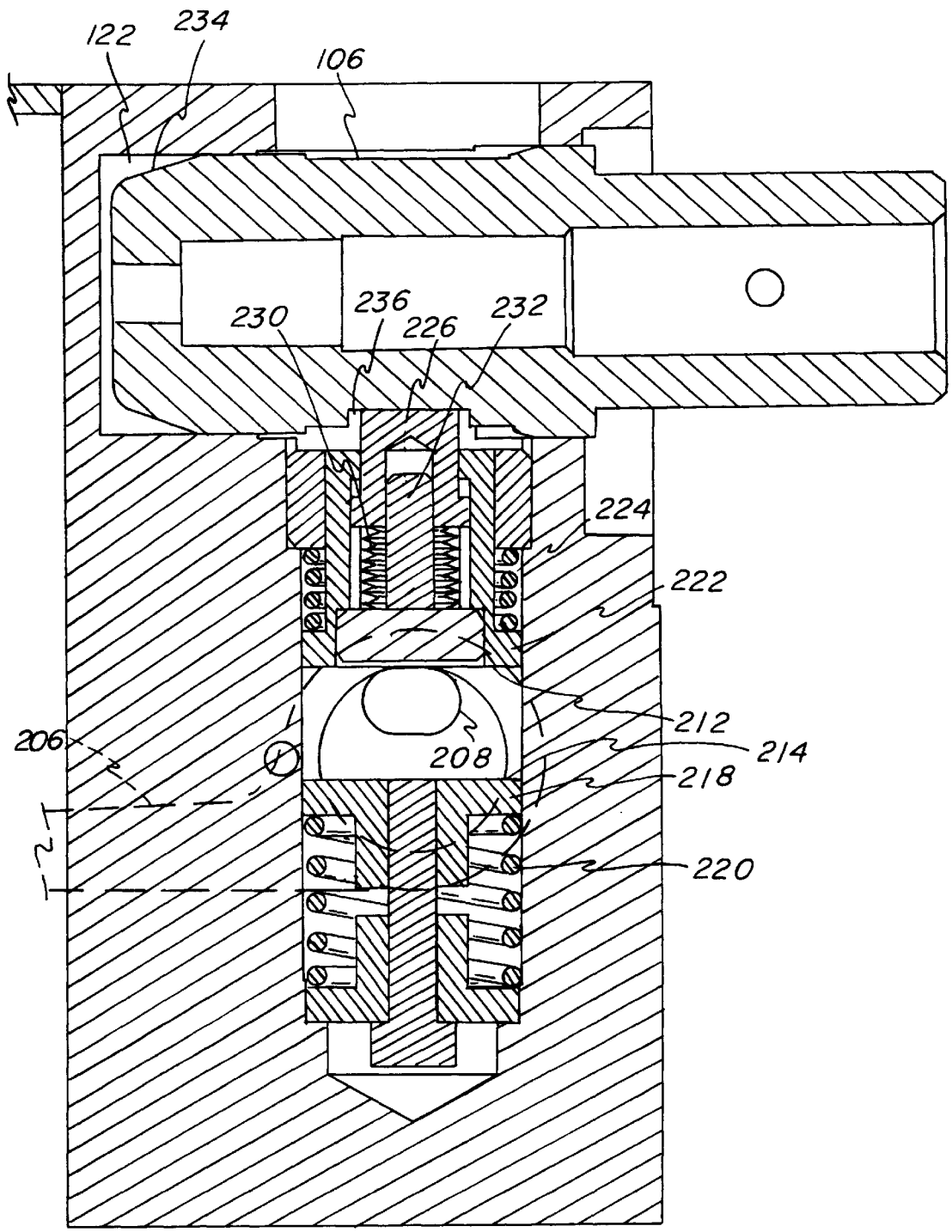

To further ensure that the pin 106 remains firmly located within the aperture 122, the lever 206 may be rotated upwardly to the position shown in FIG. 27 whereby the cam 208 acts on the upper shelf 212 to push the plunger assembly 210 upwardly whereby the belleville washer spring 230, as well as the spring 224, is compressed to provide a predetermined compressive force for moving the latch pin 226 upwardly into firm engagement with the pin 106. In this manner, the pin 106 is immovably locked within the aperture 122 to positively position the leg section 20 on the end of the seat section 18.

Figure 28:
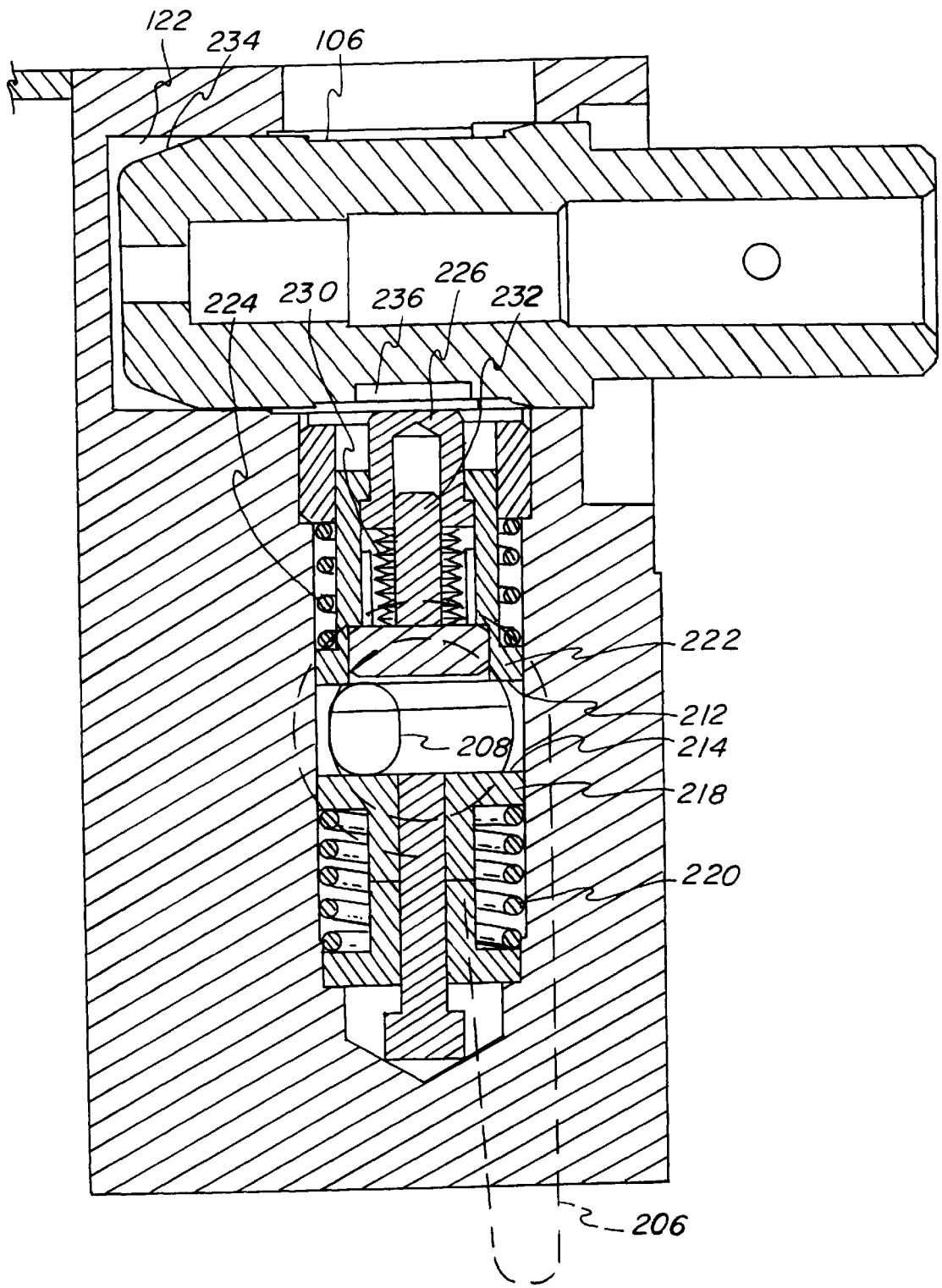

When it is desired to remove the pin 106 from the aperture 122, the lever 206 may be moved to the position shown in FIG. 28. In this position, the cam 208 acts on the lower shelf 214 to move the plunger assembly 210 downwardly against the force of the spring 220 whereby the latch pin 226 is moved out of engagement with the slot 236. With an operator thus holding the lever 206 in its downward position, the pin 106 may be extracted from the aperture 122 to thereby separate the leg section 220 from the seat section 18. It should be understood that a similar latch mechanism is provided for the opposite aperture 124 of the seat section 18 and operates in a manner similar to that described above.

In addition, it should be understood that the pin mounting points 38, 40 on the back section 16 and 110, 112 on the leg section 20 may also be provided with latching mechanisms similar to the latching mechanism described above. In the preferred embodiment of the latching mechanisms for the pin mounting points 38, 40 and 110, 112 the latching mechanisms do not automatically latch the sections in place. Rather, they are formed similar to the above-described latching mechanism but without the spring 220 to bias the plunger assembly 210 upwardly such that the latching mechanisms will operate to retain pins therein only by movement of an associated lever to the locking position shown in FIG. 27. Further, in such a latching mechanism, an additional movement of the lever is preferably provided to prevent inadvertent movement of the lever. For example, the lever may be provided with a lateral outward movement wherein the lever must be pulled outwardly before it may be rotated.

It should be noted that by providing a removable leg section 20 the present surgical table 110 provides additional room for accommodating the C-arm of an x-ray apparatus and further provides sockets which may be used for mounting additional accessories when the leg section 20 is not in place. Examples of such accessories include attachments for shoulder arthroscopy, orthopedic extensions and split leg sections.

Referring to FIGS. 29–32, a side extender assembly 238 is shown for providing additional width for the surgical table 210. The side extender assembly is adapted to be used in conjunction with side rails, such as back section side rail 240 and seat section side rail 242 (FIG. 1), and a plurality of the extender assemblies 238 may be used located along the length of the table 10, as seen in FIG. 3). Specifically, the side extender assembly 238 may be mounted to a rail 242 for extending the width of the surgical table 10, as seen in FIG. 29.

Referring to FIG. 30, the extender assembly 238 includes a frame 244 for supporting a cushion 246 wherein the frame is formed as a hollow member having a passage 248 for receiving an x-ray panel therethrough. It should be noted that the table 10 of the present invention is provided with elevated panels for supporting patient receiving cushions wherein x-ray panels may be passed between the frame of the table and the support panel, as may be seen for example at 14a, 16a, 18a and 20a in FIGS. 23 and 24.

The extender assembly 238 further includes support legs 250, 252 defining rail receiving apertures 254, 256, respectively. As seen in FIG. 32, a tang 258, 260 defining an upper portion of the apertures 254, 256 is adapted to extend over and behind the rail 242. Threaded studs 262, 264 having tapered heads 263, 265 are provided extending through threaded apertures 266, 268 in the respective legs 250, 252. The studs 262, 264 are each provided with a drop handle 270, 272 mounted to the studs by pivot pins 274. As may be best seen in FIG. 32, the tapered heads 263, 265 of the studs 262, 264 are adapted to engage a lower rear edge of the rail 242 to thereby wedge the legs 250, 252 into firm engagement with the rail 242 in order to lock the side extender assembly 238 against movement.

Further, thumb screws 276, 278 extend in threaded engagement laterally through the legs 250, 252, and each includes a pad 280, 282 on a distal end thereof for contacting a side portion of the table 10. Thus, after the studs 262, 264 have been tightened into engagement with the rail 242, the thumb screws 276, 278 are turned into the legs 250, 252 to cause the pads 280, 282 to firmly engage the side of the table to thereby resist any moment forces which may tend to pivot the extender assembly 238 relative to the rail 242.

In addition, it should be noted that the extender assembly 238 includes a side rail 284 mounted to the frame 244 by screws 286 and held in a predetermined spaced relation to the frame 244 by spacers 288. Thus, although the side extender assembly 238 of the present invention is mounted to one of the rails 240, 242 of the surgical table 10 such an arrangement does not eliminate the provision of a side rail for mounting accessories to the table 10.

It should be apparent from the above description that the side extender assembly 238 provided for the surgical table 10 of the present invention is configured such that it permits use of the table in a manner similar to that when the extender assembly is not present. In particular, it permits the use of x-ray panels which may be inserted through the extender assembly 238 as well as permitting the use of accessories to be mounted to the side rail 284 of the assembly 238.

Further, from the above description, it should be apparent that the present surgical table includes a control system for facilitating operator manipulation of the table. By providing a control system which responds to the particular configuration of the table, the possibility of error or inconvenience introduced by requiring the operator to manually input to the controller the particular mode of operation for the table is minimized. In addition, it should be apparent that the present surgical table facilitates movement of the table sections by providing a return to neutral function for the different selectable functions of the controller and by providing a mechanism for manipulating the leg section to optimize the forces required for each position of the leg section.

While the form of apparatus herein described constitutes a preferred embodiment of this invention, it is to be understood that the invention is not limited to this precise form of apparatus, and that changes may be made therein without departing from the scope of the invention which is defined in the appended claims.

What is claimed is:

1. A surgical table comprising:

a table top, said table top including a movable portion;

a support for supporting said table top;

an actuator for moving said table top relative to said support;

a controller having selectable functions for energizing said actuator to move said table top to predetermined positions in a normal mode of operation when said surgical table is in a first configuration, and having a reverse mode of operation for reversing said selectable functions in a second configuration of said surgical table said movable portion of said table top being movable to reconfigure said surgical table from said first configuration to said second configuration; and including a sensor system located on said table for sensing engagement of said movable portion with said surgical table, and said selectable functions of said controller changing from said normal mode to said reverse mode of operation in response to said sensor system sensing engagement and disengagement of said movable portion to and from said table top.

2. The surgical table as recited in claim 1 wherein said movable portion of said table top comprises a patient support portion.

3. The surgical table as recited in claim 1 wherein said table top comprises a plurality of sections for supporting a patient, one of said plurality of sections comprising said movable portion, and movement of said movable portion relative to at least one other of said sections causes said surgical table to be reconfigured into said second configuration.

4. The surgical table as recited in claim 3 wherein said plurality of sections includes a back section, a head section mountable to said back section in said first configuration, a seat section connected to said back section and a leg section connected to said seat section, said head section defining said movable portion and being mountable to said leg section in said second configuration.

5. The surgical table as recited in claim 4 wherein said sensor system is connected to said controller for sensing the location of said head section on said surgical table.

6. The surgical table as recited in claim 3 wherein said movable portion is attachable to said table top at a first location and a second location, said sensor system being operable to sense the location of said movable portion whereby said controller is activated to reverse said selectable functions.

7. The surgical table as recited in claim 1 wherein said sensor system includes sensors located at opposing ends of said table and said movable portion of said table top is mountable to either of said opposing ends said sensors being operable for sensing the location of said movable portion at either end of said table top.

8. The surgical table as recited in claim 7 wherein said selectable functions are reversed in response to a sensed position of said movable portion of said table top being changed.

9. The surgical table as recited in claim 1 wherein said selectable functions comprise trendelenburg, lateral tilt and flex movements for said table top.

10. A surgical table comprising:
   an articulated table top including a plurality of interconnected sections;
   a system of actuators for moving said sections;
   a controller having selectable functions for energizing said actuator system to move said sections in a normal mode of operation and having a reverse mode of operation wherein said selectable functions are reversed;
   wherein at least one of said sections is movable from a first position defining a first configuration to a second position defining a second configuration on said surgical table, and movement of said at least one section from said first position to said second position causes said controller to operate in said reverse mode of operation; and
   including sensors located at said first and second positions wherein said sensors are operable for sensing the location of said at least one section and for actuating said controller to operate in either said normal or reverse mode of operation.

11. The surgical table as recited in claim 10 wherein said at least one section comprises a head section.

12. The surgical table as recited in claim 10 wherein said sensors include switches associated with apertures located at first and second ends of said table top corresponding to said first and second positions, and said at least one section includes pins for engaging within said apertures, said pins being operable to actuate said switches.

13. The surgical table as recited in claim 10 wherein at least two of said sections are movably mounted to said surgical table, and said first and second positions are located at opposing ends of said table.

14. The surgical table as recited in claim 13 wherein said at least two sections comprise a head section and a leg section.

15. The surgical table as recited in claim 10 wherein said plurality of sections includes a back section, a head section mountable to said back section in said first configuration, a seat section connected to said back section and a leg section mountable to said seat section, said head section further being mountable to said leg section in said second configuration.

16. The surgical table as recited in claim 15 wherein said leg section is further mountable to said seat section at a location opposite said back section.

17. A surgical table comprising:
    a table top;
    a support for supporting said table top;
    an actuator system for moving said table top relative to said support;
    a controller including a plurality of function buttons which are manually operable and define selectable functions for energizing said actuator system to move said table top; and
    wherein actuation of at least one of said function buttons energizes said actuator system to move a predetermined portion of said table top in a predetermined direction to a predetermined neutral position where said controller automatically deactivates said actuator system to terminate movement of said predetermined portion, and wherein release and further actuation of said at least one function button energizes said actuation system to move said predetermined portion in said predetermined direction past said neutral position.

18. The surgical table as recited in claim 17 wherein said table top comprises a plurality of sections, said predetermined portion forming one of said sections, and said neutral position corresponds to said predetermined portion being aligned substantially parallel to an adjacent section.

19. The surgical table as recited in claim 17 wherein said table top comprises a back section, a seat section and a leg section, said seat section being movable independently of said back section and said leg section being movable independently of said seat section.

20. The surgical table as recited in claim 19 wherein said predetermined portion comprises said seat section and said neutral position corresponds said seat section being aligned substantially parallel to said back section.

21. The surgical table as recited in claim 19 wherein said predetermined portion comprises said leg section and said neutral position corresponds to said leg section being aligned substantially parallel to said seat section.

22. The surgical table as recited in claim 17 wherein said selectable functions include lateral left and right tilt functions and said neutral position corresponds to said table top being level in a lateral direction.

23. The surgical table as recited in claim 17 wherein said selectable functions include trendelenburg and reverse trendelenburg functions and said neutral position corresponds to said table top being level in a longitudinal direction.

24. A surgical table comprising:
    an articulated table top including a plurality of interconnected sections mounted for pivotal movement relative to each other;
    a support for supporting said table top;
    an actuator system for moving said sections;
    a controller including a plurality of function buttons which are manually operable and define selectable functions for energizing said actuator system to move said sections; and
    wherein actuation of at least one of said function buttons energizes said actuator system to move at least one of said sections in a predetermined direction to a predetermined neutral position where said controller automatically deactivates said actuator system to terminate movement of said at least one section, and wherein release and further actuation of said at least one actuation button energizes said actuation system to move said at least one section in said predetermined direction past said neutral position.

25. The surgical table as recited in claim 24 wherein said sections include a back section, a seat section adjacent to said back section, and a leg section adjacent to said seat section, said controller being operable for actuating said seat section for movement independently of said back section and for actuating said leg section for movement independently of said seat section.

26. The surgical table as recited in claim 25 wherein movement of said seat section is automatically terminated when said seat section is substantially parallel to said back section and movement of said leg section is automatically terminated when said leg section is substantially parallel to said seat section.

27. A surgical table comprising:
an articulated table top including a back section, a seat section and a leg section, said seat section being pivotally mounted relative to said back section and said leg section being pivotally mounted relative to said back section;
a support for supporting said table top;
a system of actuators for moving said sections of said table top;
a controller for energizing said system of actuators, said controller having a normal mode of operation and a reverse mode of operation; and
said controller being operable to energize said system of actuators to configure said table in flex and reflex positions wherein a flex/reflex point in said normal mode of operation is located between said back and said seat sections and a flex/reflex point in said reverse mode of operation is located between said seat and said leg sections.

28. The surgical table as recited in claim 27 wherein said table top is adapted to be reconfigured and said controller automatically operates in said reverse mode of operation in response to said table top being reconfigured.

29. The surgical table as recited in claim 28 wherein said table top includes a removable section adapted to be alternately located at a head end and a foot end of said table top said controller automatically operating in said reverse mode of operation in response to said removable section being mounted at said foot end of said table top.

30. A surgical table comprising:
a table top including at least a seat section and a leg section mounted to said seat section;
a support for supporting said table top;
an actuator for driving said leg section in pivotal movement relative to said seat section from a raised position approximately 80° above a plane defined by said seat section to a lowered position approximately 105° below said plane; and
wherein a force applied to said leg section during said pivotal movement varies such that forces applied by said actuator to said leg section to raise and lower said leg section between the plane defined by the seat section and said raised position are greater than forces applied by said actuator to said leg section to lower and raise said leg between the plane defined by the seat section and said lowered position.

31. The surgical table as recited in claim 30 wherein said actuator includes a slide mounted for sliding movement along a predetermined path on said seat section, a linkage having a first end connected to said leg section and a second end connected to said slide, and a driver for driving said slide along said predetermined path.

32. The surgical table as recited in claim 31 wherein said predetermined path is linear.

33. The surgical table as recited in claim 31 wherein said predetermined path extends non-parallel to said plane.

34. The surgical table as recited in claim 33 wherein said predetermined path extends downwardly in a direction toward said leg section.

35. The surgical table as recited in claim 31 wherein said driver comprises a power cylinder.

36. The surgical table as recited in claim 35 including identical actuators located on opposing sides of said surgical table, each said actuator including a fluid cylinder and said fluid cylinders being connected in fluid communication with each other whereby said cylinders exert an equal actuation force for moving said leg section.

37. The surgical table as recited in claim 30 wherein said leg section is a unitary member spanning substantially the entire width of said surgical table, said leg section being detachable from said seat section.

38. A surgical table comprising:
a table top including at least a first section and a second section detachably connected to said first section;
a support for supporting said table top;
a latch mechanism for retaining said second section in engagement with said first section, said latch mechanism automatically latching said second section onto said first section in response to movement of said section into association with said first section;
means for locking said latch mechanism to prevent removal of said second section from said first section; and
wherein said second section comprises an engagement pin and said first section comprises an aperture for receiving said engagement pin, and said latch mechanism engages said engagement pin to retain said second section on said first section.

39. The surgical table as recited in claim 38 wherein said latch mechanism includes a latch pin resiliently biased into said aperture and said engagement pin includes a slot for receiving said latch pin.

40. The surgical table as recited in claim 39 wherein said latch mechanism includes a plunger assembly movable relative to said aperture and said latch pin is supported for movement with said plunger assembly, said latch pin being further supported for movement within said plunger assembly.

41. The surgical table as recited in claim 40 including biasing means within said plunger assembly for biasing said latch pin in a direction toward said aperture.

42. The surgical table as recited in claim 40 wherein said means for locking said latch mechanism comprises a lever actuated cam member located in engagement with said plunger assembly for biasing said plunger assembly toward said aperture whereby said engagement pin is firmly locked within said aperture.

43. The surgical table as recited in claim 42 wherein said lever is mounted for rotation and rotation of said lever in a first direction causes said plunger assembly to move toward said aperture, and rotation of said lever in a second opposite direction causes said plunger assembly to move away from said aperture whereby said latch pin is moved out of engagement with said slot.

44. A surgical table comprising: a table top;
a support for supporting said table top;
an actuator for moving said table top relative to said support;
control means for energizing said actuator;
a pump system for supplying pressurized fluid to said actuator, said pump system comprising a first pump and a second pump;

wherein said control means is operable to energize said first pump to supply pressurized fluid to said actuator as long as said first pump is operable, and said control means is operable to energize said second pump in the event said first pump becomes inoperable; and wherein said control means comprises first and second controllers having substantially identical function selection switches, said first controller being operable to energize said first pump as long as said first pump is operable, and only said second controller being operable to energize said second pump in the event said first pump becomes inoperable.

45. The surgical table as recited in claim 44 wherein said pump system includes first and second motors for driving said first and second pumps, respectively.

46. The surgical table as recited in claim 45 wherein said pump system includes a fluid reservoir containing said first and second pumps, and said motors are located outside of said reservoir.

* * * * *